United States Patent [19]
Brent et al.

[11] Patent Number: 5,852,169
[45] Date of Patent: Dec. 22, 1998

[54] MAX-INTERACTING PROTEINS AND RELATED MOLECULES AND METHODS

[75] Inventors: Roger Brent, Cambridge; Antonis S. Zervos, Boston, both of Mass.

[73] Assignee: The General Hospital Corporation, Boston, Mass.

[21] Appl. No.: 462,498

[22] Filed: Jun. 5, 1995

Related U.S. Application Data

[62] Division of Ser. No. 11,398, Jan. 29, 1993, Pat. No. 5,512,473.

[51] Int. Cl.⁶ .................................................. C07K 14/47
[52] U.S. Cl. ......................... 530/350; 530/300; 530/324; 530/326
[58] Field of Search ..................... 530/350, 326, 530/300, 324

[56] References Cited

U.S. PATENT DOCUMENTS

| | | | |
|---|---|---|---|
| 5,302,519 | 4/1994 | Blackwood et al. | 435/69.1 |
| 5,512,473 | 4/1996 | Brent et al. | 435/240.2 |
| 5,624,818 | 4/1997 | Eisenman et al. | 435/69.1 |
| 5,663,313 | 9/1997 | Hawkins et al. | 536/23.1 |

OTHER PUBLICATIONS

Grankowski et al. Isolation and characterization of recombinant human casein kinase II subunits and from bacteria. European Journal of Biochemistry. vol. 198, No. 1, pp. 25–30, May 23, 1991.

Balckwood et al. Max: a helix–loop–helix zipper protein that forms a sequence–specific DNA–binding complex with Myc. Science. vol. 251, pp. 1211–1217, Mar. 8, 1991.

Berberich et al. Casein kinase II inhibits the DNA–binding activity of Max homodimers but not Myc/Max heterodimers. Genes and Development. vol. 6, No. 2, pp. 166–176, Feb. 1992.

Zervos et al. Cell. vol. 72, pp. 223–232, Jan. 29, 1993.

Alvarez et al. The Journal of Biological Chemistry. vol. 266, pp. 15277–15285, 1991.

Barret et al. Molecular and Cellular Biology. vol. 12, pp. 3130–3137, 1992.

Beckman et al. Genes and Development. vol. 5, pp. 1057–1066, 1991.

Blackwell et al. Science. vol. 250, pp. 1149–1151, 1990.

Blackwood et al. Genes and Development. vol. 6, pp. 71–80, 1992.

Blackwood et al. Current Opinions in Genetics and Development. vol. 2, pp. 227–235, 1992.

Crews et al. Cell Growth and Differentiation. vol. 3, pp. 135–142, 1992.

Dang et al. Proceedings of the National Academy of Sciences, USA. vol. 89, pp. 599–602, 1992.

Golemis et al. Molecular and Cellular Biology. vol. 12, pp. 3006–3014, 1992.

Halazonetis et al. Science. vol. 255, pp. 464–466, 1992.

Kato et al. Genes and Development vol. 6, pp. 81–92, 1992.

Kato et al. Molecular and Cellular Biology. vol. 10, pp. 5914–5920, 1990.

Kerkoff et al. Proceedings of the National Academy of Sciences, USA. vol. 88, pp. 4323–4327, 1991.

Lech et al. Cell. vol. 52, pp. 179–184, 1988.

Luscher et al. Molecular and Cellular Biology. vol. 8, pp. 2504–2512, 1988.

Papoulas et al. The Journal of Biological Chemistry. vol. 267, pp. 10470–10480, 1992.

Prendergast et al. Cell. vol. 65, pp. 395–407, 1991.

Prednergast et al. Science. vol. 251, pp. 186–189, 1991.

Hann et al. Molecular and Cellular Biology. vol. 4, p. 2486–2497, 1984.

(List continued on next page.)

*Primary Examiner*—Elizabeth C. Kemmerer
*Assistant Examiner*—Brian Lathrop
*Attorney, Agent, or Firm*—Clark & Elbing LLP

[57] ABSTRACT

Disclosed are substatially pure preparations of Max-Interacting (Mxi) polypeptides, DNA encoding such polypeptides, antibodies recognizing such polypeptides, and diagnostic and therapeutic methods utilizing such polypeptides.

6 Claims, 7 Drawing Sheets

```
                 *
NRSTHNELEKNRRAHLRLCLERLKVLIPLGPDCT-RHTTLGLLNKAKAHIKKLEEA---ERKSQHQLENLEREQRFLKWRLEQL   MXI 1
KRRTHNVLERQRRNELKLSFFALRDQIPEVANNE-KAPKVVILKKATEYVLSIQSD---EHRLIAEKEQLRRRREQLKHKLEQL   v-MYC
KRRTHNVLERQRRNELKRSFFALRDQIPELENNE-KAPKVVILKKATAYYLSVQAE---EQKLISEEDLLRKRREQLKHKLEQL   c-Myc
RRRNHNILERQRRNDLRSSFLTLRDHVPELVKNE-KAAKVVILKKATEYVHSLQAE---EHQLLLEKEKLQARQQQLLKKIEHA   N-myc
KRKNHNFLERKRRNDLRSRFLALRDQVPTLASCS-KAPKVVILSKALEYLQALVGA---EKRMATEKRQLRCRQQQLQKRIAYL   L-myc
KRAHHNALERKRRDHIKDSFHSLRDSVPSLQGQ--KASKAQILDKATEYIQYMRRK---NHTHQQDIDDLKRQNALLEQQVRAL   Max
RREIANSNERRRMQSINAGFQSLKTLKPHTDGE--KLSKAAILQQTAEYIFSLEQE---KTRLLQQNTQLKRFIQELSGSSPKR   AP-4
KKDNHNLIERRRRFNINDRIKELGTLIPKSSDPQMRWNKGTILKASVDYIRKLQKEQQSKDRLESRQRSLEQANRSLQLRIQEL   TFE-3
```

BASIC REGION    HELIX I    HELIX II    LEUCINE ZIPPER

OTHER PUBLICATIONS

Vinson et al. The New Biologist. vol. 4, pp. 396–403, 1992.

Zervos et al. Mxi2, a mitogen–activated protein kinase that recognizes and phosphorylates Max protein. Proceedings of the National Academy of Sciences, USA, vol. 92, pp. 10531–10534, Nov. 1995.

Han et al. A MAP kinase targeted by endotoxin and hyperosmolarity in mammalian cells. Science. vol. 265, pp. 808–811, Aug. 5, 1994.

Lee et al. A protein kinase involved in the regulation of inflammatory cytokine biosynthesis. Nature. vol. 372, No. 22, pp. 739–746, Dec. 29, 1994.

Han et al. Endotoxin induces rapid protein tyrosine phosphorylation in 7OZ/3 cells expressing CD14. The Journal of Biological Chemistry. vol. 268, No. 33, pp. 25009–25014, Nov. 25, 1993.

Fig. 2 (SEQ ID NO: 1 AND 2)

```
AGATTATGATCGCCTGAGGCCCCTCCTGAGCCCAGATACCGATGTTATACTGATGTGTTTTCCTTTTTTTTTTTTTTAAGTAATTAAGGGTAGTTAAATTATTTAAAGTATACA  120
AAGTCCAAACAGCCAGGGGTAAGGTCTCCAAGAGGCCTTCCCAGGGTAAGGAGTGCGGAGAGGGCCCCGGTGCCCACCCGGGTGCCATGAGCCCGTGAAGATGATCAACGTGCAGCG  240
                                                                                                M  P  S  P  R  L  Q  H  S  K  P  P  R  R  L    15
TCTGCTGGAGGCTGCCGAGTTTTGGAGCCGCGGAGCGAGAGTGTGAACATCGTACGCCTCTTCATTCCCGTCCAGCCTCCAGCTGCAGCATTCAAAGCCTCAAAGCCCCACGGAGGTTG  360
 S  R  A  Q  K  H  S  S  G  T  S  N  T  S  T  A  N  R  S  T  H  N  E  L  E  K  N  R  R  A  H  L  R  L  C  L  E  R  L  K    55
AGCCGGGCACAGAAACACAGCAGCGGGACAGCGAGCGAGTGTGAACATCTACGCCAACATGAGCTGGAAAAGAATCGTGAAAAGAATCTGCGCCTTGTTTAGAACGCTTAAAA  480
 V  L  I  P  L  G  P  D  C  T  R  H  T  T  L  G  L  L  N  K  A  K  A  H  I  K  K  L  E  E  A  E  R  K  S  Q  H  Q  L  E    95
GTTCTGATTCCACTAGGACCAGACTGCACTAGGCACACCACCCTGGGTTTGCTCAACAAAGCCAAAGCTCACATCAAGAAACTGGAAGAAGCTGAAAGAAAAAGCCAGCACCAGCTCGAG  600
 N  L  R  E  Q  R  F  L  K  W  R  L  E  Q  L  Q  G  P  Q  E  M  E  R  I  R  M  D  S  I  G  S  T  I  S  S  D  R  S  D     135
AATTTGAACGAGCAGAGATTTTTAAAGTGGCGACTGGAACAGCTGCAGGGTCCTCAGGAGATGGAACGAATACGAATGGACAGCATTGGATCAACATATTCTTCAGATCGTTCTGAT  720
 S  E  R  E  E  I  E  V  D  V  E  S  T  E  F  F  S  H  G  E  V  D  N  I  S  T  T  S  I  D  D  H  S  S  L  P  S  I         175
TCAGAGCGAGAGGAGATTGAAGTGGATGTTGAAAGCACAGAGTTCTTCCCATGGAAGCACAGAGTGGACAATATAAGTACCACCAGCATCGATGACCATCAGCAGCCTGCCGAGTATT  840
 V  Q  G  K  I  F  T  G  P  I  Q  Y  K  Q  S                                                                               215
                                                                                                                           ?
GTTCAGGGCAAAATATTCACTGGSCCAATTCAATACAAACAATCT  
 G  S  D  E  G  Y  S  S  A  S  V  K  L  S  F  T  S  Y  R  T  Q  H  D  I  T  V  Q  G  K  I  F  T  G  P  I  Q  Y  K  Q  S   215
GGGAGTGACGAGGGTTACTACTCCGCAGTCTCCAGTGTCAAACTTTCATTCACTTCTTATAGAACCCAGCATGACATTACAGTGCAGGGCAAAATATTCACTGGCCCAATTCAATACAAACAATCT  960
 L  K  L  G  S  *                                                                                                           220
CTTAAATTGGTTCATGATGCAGTCAGTCCTGCTCCTTTAAACAAACAAACTATACTTGAACATGAACAAAACAAATTTTTTAAAGCAAATTAGCAAAAGTGGGGC  1080
AGAGCTCCCAAGGAGAACAAATATTCAGAATATATTGCTCATACTACATTGAGTTGACACATTTGAAAATTTCCTGAGCTTTATGGGTCCTAAAAGCAAAATAAAAACTATT  1200
GAGATGCCATCCTCTCTTGTTCTCTTTCGTTTCGATTTCTTCATATACATTTGGACATAGTAATGAGCTATTAAAGCACATAATCTTATTATTATTT  1320
CGAATGAAAAGACAAGAAAAATCAGGTAGCTCATTGTCTGCAAAAGGAGGAGACTCCATGAAAGGATCATCATGAGCAGCTTCGTGTTGGATTCCATGCTAAGCAAGCTAACCT  1440
TTTTTTGAAAAAGCTCAACAGAGATTTCAAAAAGAGACTTTTGTAGGCCACACATGGGAGACTGTTGCACCTCTCATCATGACAGCAGATTAGCCTATGAGTATGGATT  1560
TATCCTGCATTGTTAGCACTAGGACAAAAGTCCACCTGCCTCTTTGTCTGCAAGTTGCACGCAGATTAGCCTGCCAGCCTATGAGTATGGATTTATTTCAGATTTTGA  1680
GGGGGGGCAAAAGGAAAAAGCTCAAACCAAAATGACATCTTTTAAAGCCATTATCCATAAAAATCATAAAAATGAAATGAGGTCTTTATAGTGCAAAATGAAAAAAATCATCTATTTTGATGCA  1800
TAACTGTTTTATATGTGTTGAAAACATTTCATCACTTCACTCTTTATAGTGCAAAAATCAAATGAAAGGTCTGGGCTAGTTCAGGTAGAAAAAGGGTCAATGCTATTTTGTTTTAGAATCATTACCTTTTA  1920
GCATTTGATAATGATAAAAACACCTCACACTTCACTTGAAGAGAAAACACTAATGTCAATGCTATTTTGTTTTAGAATCATTACCTTTTA  2040
CCAGCTTTTTAACCATCTGATATCTGCACTGTGCAGTGCTATTGTTCAGGTGCCCACTGTGCCCCTCCTGTATTGTTACTCTTGTTACTCTTAAGTATGTTATTTCAGTATCCTGACCTTGATGTCATGTGTCCCTTTGTC  2160
TCTTCCTCACAGTTCCCCACTGTCCCCTGTGCAGGTACATATAGCACTATGTGAGACCTTACCCTCCCTCTCCCTTTGGACCCTTTGTATACTTGTAACTTAAATAATTTAACTT  2280
TTTCAAACTTCCAAGGTTCCCCTGCCCCTCCCCTCTCCCTTTGGACCCTTTGTATACTTGTAAATAATTTAACTTTGTATACTTGTTAATTAACTTTAATTACT  2400
TAAAAAAAAAAAAAAA   2417
```

Fig. 2

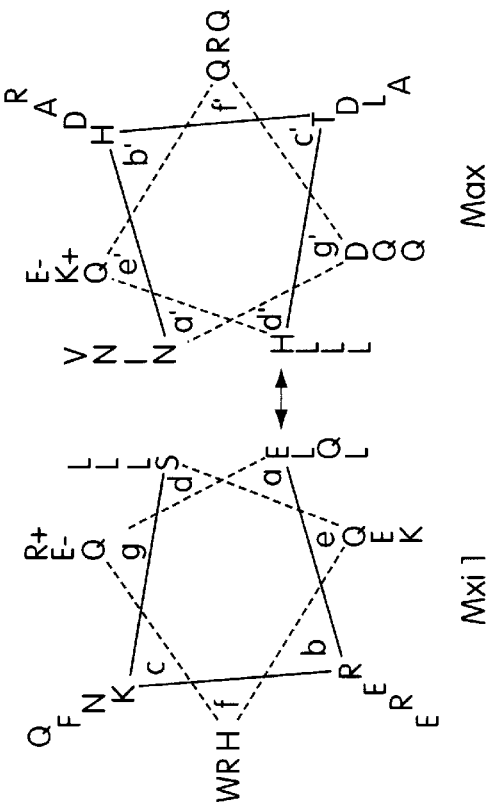

Fig. 7

```
agtgaattgtaatacgactcactataggggcgaattgggtaccggcccccctcgagtgtcgacgttatcgataagcttgatatcgaattcccgcggccgcgcgcgatctcgggtcgcggc  120
agccgcacctgcgcgggcgaccagcgcaaggtcccgccgctgggcggcagcaaggcccggggagaggtgcgggtgcaggcgggccccacaggcgccacctcttgccgcgcg          240
tgccgctggaaatgtctcaggagagcccacgttctacaccggagaggctgaacaagacaatctggagagctgccgagcttgccagcgtgcccagcgttaccagacctgtctccagtggctctggcgctatggc  360
              M  S  Q  E  R  P  T  F  Y  R  Q  E  L  N  K  T  I  W  E  V  P  P  E  R  Y  Q  N  L  S  P  V  G  S  G  A  Y  G    36
tctgtgtgctgtttgacacaaaaacgggttacgtgtggcagtgaagaagtctctccagacctcatcattcatgaaaagaactacagagaactgcggttacttaaa                480
S  V  C  A  A  F  F  D  T  K  T  G  L  R  V  A  V  K  K  L  S  R  P  F  Q  S  I  I  H  A  K  R  T  Y  R  E  L  R  L  L  K   76
catatgaaacatgaaaatgtgattgtctgttgacgtttttacacctgcaaggtctctggaggaattcaatgatgtgtatctgtgaccatctcatggggcagatctgaacaacatt         600
H  M  K  H  E  N  V  I  G  L  L  D  V  F  F  T  P  A  R  S  L  E  E  F  N  D  V  Y  L  V  T  H  L  M  G  A  D  L  N  N  I  116
gtgaaatgtcagaagcttacagatgaccatgtccagttccttatctaccaaattctccgaggtctaaagtatatacattcagctgacataattcacaggaccatatttcag tcaaaccctagtgctgaac  720
V  K  C  Q  K  L  T  D  D  H  V  Q  F  L  I  Y  Q  I  L  R  G  L  K  Y  I  H  S  A  D  I  I  H  R  D  L  K  P  S  N  L  156
gctgtgaatgaagactgtgagctcaagattctgatttttggactggcctcggccacacagatgataatgccgagctgttgactggaagaacattgttcctggtacagacccatattgtcagttgaagctcatttta  840
A  V  N  E  D  C  E  L  K  I  L  D  F  G  L  A  R  H  T  D  D  E  M  T  G  Y  V  A  T  R  W  Y  R  A  P  E  I  M  L  N  196
tggatgcattacaaccagacagttgatatttggagtcagtggatgcataatgccgagctgttgactggaagaacattgtttcctggtacagacccatattgtcagttgaagctcatttta  960
W  M  H  Y  N  Q  T  V  D  I  W  S  V  G  C  I  M  A  E  L  L  T  G  R  T  L  F  P  G  T  D  H  I  D  Q  L  K  L  I  L  236
agactcgttgaacccagggggctgagctttgaagaaaatctcctcagagtctgcaagtttctatattcagtctttgactcagatgccgaagatgaactttgcgaatgtattattggt  1080
R  L  V  G  T  P  G  A  E  L  L  K  K  I  S  S  E  S  A  S  F  Y  I  Q  S  L  T  Q  M  P  K  M  N  F  A  N  V  F  F  I  G  276
gccaatccctgggtaagttgaccatatatctcacctcatgataattggttatgataaattgggatttgaagaagagtttctcctttgaccaaataaagtaccattatga          1200
A  N  P  L  G  K  L  T  I  Y  P  H  L  M  D  I  E  L  V  M  I  *  297   (SEQ ID NO: 3 AND 4)
```

's,852,169

MAX-INTERACTING PROTEINS AND RELATED MOLECULES AND METHODS

This is a divisional of application Ser. No. 08/011,398, U.S. Pat. No. 5,512,473, filed Jan. 29, 1993.

BACKGROUND OF THE INVENTION

This invention relates to cancer diagnostics and therapeutics.

Members of the Myc protein family are involved in the formation of many cancers; in model systems, their heightened expression can induce oncogenic transformation (for reviews, see Cole, Genet 20:361–384, 1986; Lüscher and Eisenman, Genes and Development 4:2025–2035, 1990) and apoptosis (Evan et al., 1992; Cell 69:119–128, 1992; Shi et al., Science 257:212–214, 1992), and it can block differentiation (Freytag, Mol. Cell. Biol. 8:1614–1624, 1988; Miner and Wold, Mol. Cell Biol. 11:2842–2851, 1991). Of the Myc proteins, the best studied are probably the c-myc and v-myc products (cMyc and vMyc). These proteins are localized to the nucleus (Dang and Lee, Mol. Cell. Biol. 8:4048–4054, 1988) and activate transcription in transfection experiments when brought to DNA by heterologous DNA binding domains (Lech and Brent, Cell 52:179–184, 1988; Kato et al., Mol. Cell. Biol. 10:5914–5920, 1990; Golemis and Brent, Mol. Cell. Biol. 72:3006–3014, 1992). These proteins contain an activation domain in their amino terminus whose integrity is correlated with Myc's ability to cause oncogenic transformation (Kato et al., 10:5914–5920, 1990; Barrett et al., Mol. Cell. Biol. 12, 3130–3137, 1992). The proteins also contain a conserved structure, the basic region helix loop helix leucine zipper (hHLH-Zip) (reviewed in Vinson and Garcia, The New Biologist 4(4):396–403, 1992), which directs dimerization and DNA recognition (Dang et al., Proc. Natl. Acad. Sci. USA 89:599–602, 1992; Blackwell et al., Science 250:1149–1151, 1990; Halazonetis and Kandil, Science 255:464–466, 1992). These facts suggest that the biological function of cMyc and vMyc might depend on their ability to bind specific sequences and activate transcription.

This hypothesis has been greatly strengthened by the isolation of Max, a human protein that forms tight heterodimers with cMyc (Blackwood and Eisenman, Science 251:1211–1217, 1991), and the discovery of its murine homolog, Myn (Prendergast et al., Cell 65:395–407, 1991). Max was cloned using an in vitro method that depended on its ability to interact with the cMyc bHLH-Zip (Blackwood and Eisenman, Science 251:1211–1217, 1991). Max protein and mRNA are expressed in all tissues in which cMyc is expressed, and some, including the brain, in which it is not. Two different forms of the protein are encoded from differently spliced transcripts, a 151 amino acid protein (here called Max 1-151 or simply Max) and a larger form (here called Max$_{1-160}$) that contains an additional 9 amino acids at the amino terminus of the basic region. Max is localized to the cell nucleus, possibly due to a nuclear localization signal that is present at its carboxy terminus (Kato et al., Genes and Development 6:81–92, 1992). Max has a longer half life than cMyc (>24 h vs 30 min) (Blackwood et al., Genes and Development 6:71–80, 1992; Hann and Eisenman, Mol. Cell. Biol. 4:2486–2497, 1984; Luscher and Eisenman, Mol. Cell. Biol. 8:2504–2512, 1988).

Like Myc proteins, Max contains a bHLH-Zip motif. In Max, this region serves two functions; the helix loop helix and leucine zipper cause Max to form heterodimers with cMyc; and the basic region and residues near it make specific contacts with DNA. Max can form heterodimers with other members of the Myc family (Blackwood and Eisenman, Science 251:1211–1217, 1991) but does not interact with other known bHLH-Zip proteins (Blackwood and Eisenman, Science 251:1211–1217, 1991). Myc/Max heterodimers bind tightly to a consensus CACGTG sequence (Blackwood and Eisenman, Science 251:1211–1217, 1991; Prendergast et al., Cell 65:395–407, 1991). Myc/Myc homodimers bind the same sequence less tightly (Blackwell et al., Science 250:1149–1151, 1990; Prendergast and Ziff, Science 251:186–189, 1991; Kerkhoff et al., Proc. Natl. Acad. Sci. USA 88:4323–4327, 1991; Halazonetis and Kandil, Science 255:464–466, 1992; Papoulas et al., The Journal of Biological Chemistry, 267 15:10470–10480, 1992) presumably because the native protein does not form homodimers readily, so that site recognition occurs only at high protein concentrations. Phosphorylation of Max by casein kinase abolishes DNA binding by Max/Max homodimers but not by cMyc/Max heterodimers, apparently by a direct effect on Max DNA recognition (Berberich and Cole, Genes and Development 6:166–176, 1992).

Because most cMyc in vivo is associated with Max, and because cMyc/Max heterodimers bind the CACGTG site more tightly than cMyc/cMyc homodimers (Blackwood and Eisenman, Science 251:1211–1217, 1991; Prendergast et al., Cell 65:395–407, 1991), it appears likely that one of the functions of Max is to facilitate the binding of cMyc to these sites. It is also possible that association with Max modulates cMyc's gene regulatory function; consistent with this idea, we have recently shown that Max is transcriptionally inert, but that association with Myc greatly potentiates the strength of the cMyc activation function.

These facts have led to a picture of Myc and Max dependent oncogenesis, in which cMyc complexes with Max and binds to sites upstream of genes whose transcription are regulated. In this view, changes in transcription dependent on this complex could be caused by changes in site recognition, by changes in the availability of cMyc or Max, and by modifications to cMyc and Max that alter their ability to oligomerize or that affect their transcription regulatory function. Each of these modulatory steps may be regulated by other cellular proteins, including oncoproteins, which may change the expression or phosphorylation state of the proteins (reviewed in Blackwood et al., Curr. Opin. Genet. Dev. 2:227–235, 1992.

SUMMARY OF THE INVENTION

In general, the invention features a substantially pure preparation of an Mxi polypeptide. Examples of Mxi polypeptides are shown in FIG. 2 (SEQ ID NO: 2) and in FIG. 7 (SEQ ID NO: 4). Preferably, such an Mxi polypeptide is derived from a mammal, for example, a human; and is Mxi1 or Mxi2.

In a related aspect, the invention features purified DNA (for example, cDNA) which includes a sequence encoding an Mxi polypeptide, and preferably a human Mxi polypeptide (for example, Mxi1 or Mxi2). One purified Mxi-encoding DNA according to the invention is shown in FIG. 2 (SEQ ID NO: 2); nucleotides 345–1020 encode the Mxi polypeptide. Another Mxi-encoding DNA according to the invention is shown in FIG. 7 (SEQ ID NO: 4).

In other related aspects, the invention features a vector and a cell which includes a purified Mxi-encoding DNA of the invention; a purified antibody which specifically binds an Mxi polypeptide of the invention; and a method of producing a recombinant Mxi polypeptide involving, providing a cell transformed with DNA encoding an Mxi polypeptide positioned for expression in the cell; culturing the transformed cell under conditions for expressing the DNA; and isolating the recombinant Mxi polypeptide. The invention further features recombinant Mxi polypeptide produced by such expression of a purified DNA of the invention.

In yet another aspect, the invention features a method of inhibiting cell (e.g., monocytic cell) proliferation in a mammal, involving administering to the mammal a nucleic acid encoding an Mxi polypeptide, the polypeptide being positioned for expression in the mammal. Preferably, the nucleic acid is part of a retroviral vector.

In yet another aspect, the invention features a method of detecting a malignant cell in a biological sample, involving measuring Mxi gene expression in the sample, a change in Mxi expression relative to a wild-type sample being indicative of the presence of a malignancy.

In a final aspect, the invention features a method for identifying a compound which inhibits cell proliferation. The method involves contacting a candidate compound with an Mxi polypeptide of the invention and measuring Mxi activity, a change in Mxi activity being indicative of a proliferation-inhibitory compound. In preferred embodiments, the Mxi polypeptide is expressed in a recombinant cell which includes a purified Mxi-encoding DNA of the invention, and the cell or a cell extract is contacted with the candidate compound; the activity is the Mxi polypeptide's ability to interact with a Max protein (for example, as measured using the interaction trap described herein); and the activity measured is protein kinase activity (for example, as described for Mxi2).

By "Mxi polypeptide" is meant a chain of amino acids capable of interacting with a Max protein in the interaction trap system described herein. Mxi polypeptides do not include Myc, Myn or Mad proteins. Preferably, an Mxi polypeptide according to the invention is related in sequence to the Mxi polypeptides of FIG. 2 or FIG. 7.

By "substantially pure" is meant a preparation which is at least 60% by weight (dry weight) the compound of interest, e.g., an Mxi polypeptide. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an Mxi polypeptide.

By "positioned for expression" is meant that the DNA molecule is positioned adjacent to a DNA sequence which directs transcription and translation of the sequence (i.e., facilitates the production of, e.g., an Mxi polypeptide).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, e.g., Mxi-specific antibody. A purified Mxi antibody may be obtained, for example, by affinity chromatography using recombinantly-produced Mxi polypeptide and standard techniques.

By "specifically binds" is meant an antibody which recognizes and binds Mxi polypeptide but which does not substantially recognize and bind other molecules in a sample, e.g., a biological sample, which naturally includes Mxi polypeptide.

By a "malignant cell" is meant a cell which has been released from normal cell division control. Included in this definition are transformed and immortalized cells.

By "monocytic cell" is meant any cell of monocytic or premonocytic lineage.

Other features and advantages of the invention will be apparent from the following detailed description thereof, and from the claims.

DESCRIPTION OF THE DRAWINGS

FIG. 2 shows the nucleotide sequence and the deduced amino acid sequence of an Mxi1 cDNA (SEQ ID NOS: 1 and 2). The sequence of a 2417 nucleotide cDNA was determined by dideoxy sequencing of the complete sequence of two clones, the first one isolated in the yeast screen using an activation tagged HeLa expression library and encoding residues 10–220 corresponding to nucleotides 345–1020, and the second, a longer clone isolated from a HeLa library in lambda ZapII.

FIG. 3 illustrates Mxi1 bHLH-Zip. FIG. 3a shows a comparison of the bHLH-Zip region from Mxi1 residue 32 to residue 112 to bHLH-Zip regions of other proteins (SEQ ID NOS: 13–20). Amino acids present in Mxi1 and at least one other member of the set (cMyc, Max, avian vMyc, human nMyc and 1Myc, AP-4, and TFE-3) are shown in boldface. The C-terminal arginine within the basic region, which in cMyc specifies interaction with the CG core of the CACGTG consensus recognition sequence is shown with an asterisk (Halazonetis and Kandil, Science 255:464–466, 1992; Dang et al., Proc. Natl. Acad. Sci. USA 89:599–602, 1992). Sequences of the Myc family bHLH-Zip were taken from Benezra et al. (Cell 61:49–59, 1990), Max from Blackwood and Eisenmann (Science 251:1211–1217, 1991), AP-4 from Hu et al. (Genes Dev. 4:1741–1752, 1990), and TFE-3 from Beckmann et al. (Genes Dev. 5:1057–1066, 1991). FIG. 3b shows the leucine zippers of Mxi1 and Max. These leucine zippers are each shown projected onto a helical wheel as in O'Shea et al. (Science 243:538–542, 1989). Boldface indicates residues of opposite charge at the g position of Mxi1 and the e' position of Max. The arrow indicates the glutamic acid at the amino terminus of the Mxi1 leucine zipper (Mxi1 position a), which is invariant in all Myc proteins, and the histidine opposite it in Max leucine zipper position d'.

FIG. 7 shows the nucleic acid and deduced amino acid sequence of the Mxi2-encoding cDNA (SEQ ID NOS: 3 and 4).

DESCRIPTION OF THE PREFERRED EMBODIMENT(S)

We now describe the isolation and characterization of Mxi1 and Mxi2, new human proteins that form heterodimeric complexes with Max. These examples are provided for the purpose of illustrating, not limiting, the invention.

Isolation of Mxi1

Figure 1:
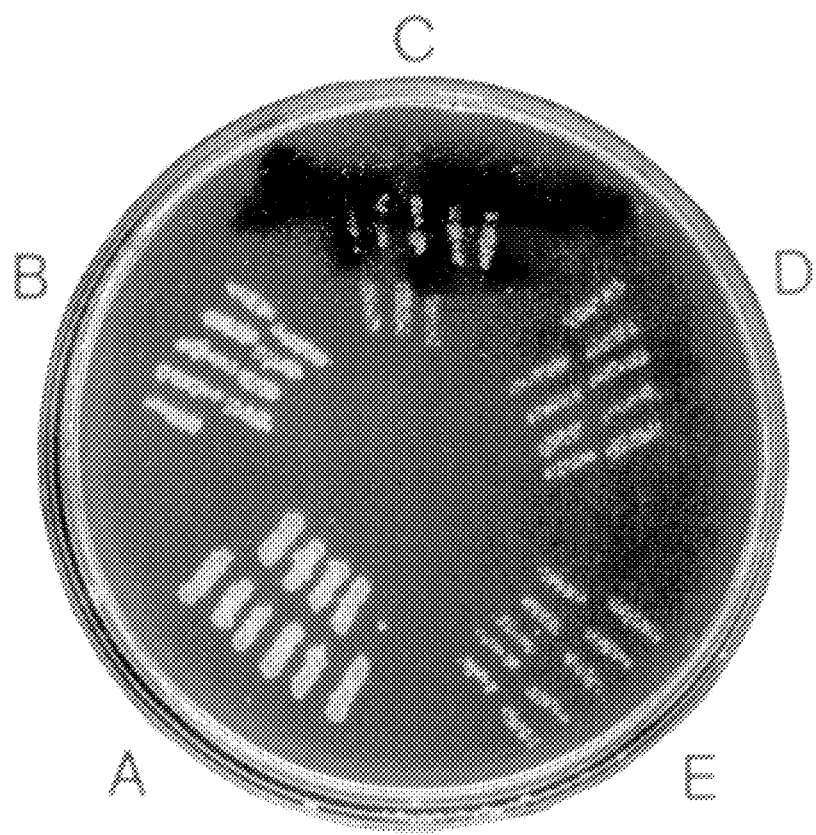
FIG. 1 shows activation by interaction of Mxi1 with different bait proteins. Individual colonies of EGY48 yeast cells that contained tagged Mxi1 (i.e., the invariant activation-tagged moiety of pJG4-5 fused to Mxi1 residues 10–220) and that also contained (A) LexA-Max, (B) LexA-cMyc-Cterm, (C) LexA-Cdc2, (D) LexA-Fus3, or (E) LexA-Bicoid were streaked with toothpicks onto a glucose ura$^-$ his$^-$ trp$^-$ master plate, and then replica plated onto a galactose ura$^-$ his$^-$ trp$^-$ leu$^-$ plate. Interaction results are indicated as activation of the LexAop-LEU2 reporter and as growth in the absence of leucine.

Mxi1 was isolated in an interaction trap system selection for proteins capable of associating with the Max protein (see below). Exactly 100 LEU+ colonies were selected from a population of yeast that derived from $7.5 \times 10^5$ library members; 80 of these colonies also showed unambiguous blue color on Xgal medium (see below). Further analysis by restriction mapping and partial sequencing revealed that many of these (62) encoded human cMyc. The rest, which in the initial screen interacted with Max to different degrees, contained new cDNAs. We selected, for further characterization, that class whose product, after cMyc, gave the strongest activation with the LexA-Max bait. We called the protein encoded by this gene Mxi1 (for Max Interactor 1). We tested the specificity of the Mxi1/Max interaction by testing the ability of Mxi1 to interact with a panel of different baits. Visual inspection of activation of the sensitive LexAop-LEU2 reporter on galactose leu$^{31}$ plates showed that Mxi1 interacted strongly with LexA-Max, detectably with LexA-cMyc-Cterm, but not with LexA-Fus3 or LexA-Bicoid (FIG. 1).

Primary Sequence

The partial Mxi1 open reading frame was sequenced on the library plasmid, which, as expected, was fused in frame to the invariant amino terminal moiety of the library encoded proteins. This cDNA was used to isolate a 2.4 kb cDNA from a commercially available HeLa cDNA library from Stratagene (LaJolla, Calif.); this cDNA was sequenced as well, and the sequence is shown in FIG. 2 (SEQ ID NOS: 1 and 2). The sequence revealed a 220 amino acid open reading frame with 315 540 flanking nucleotides and 1440 340 nucleotides. The Mxi1 open reading frame contained a bHLH-Zip region between amino acids 32–112 that was very similar in sequence to the bHLH-Zip found in Myc family proteins and in Max (FIG. 3a (SEQ ID NOS: 13–20). Compared with human cMyc, 8 out of 12 amino acids in the Mxi1 basic region are identical to those found in Myc, including the arginine at position 44, which contacts the CG core of the cMyc/Max consensus binding site. There is also substantial sequence similarity outside of this region: the Mxi1 HLH is nearly an exact match with the HLH consensus, and, as in Myc family proteins (Beckmann and Kadesch, Genes Dev. 5:1057–1066, 1991), HLH helix II is fused to the leucine zipper so that the hydrophobic heptad repeat in the zipper continues into the C terminus of helix II. Projection of the Mxi1 leucine zipper onto a helical wheel plot suggested that this region might have a favorable ionic interaction with the leucine zipper found in Max (FIG. 3b), but not with one in cMyc.

Outside of the bHLH-Zip, Mxi1 revealed no similarity to known proteins. The sequence did not reveal a classical nuclear localization signal, although arg13, arg14, lys80, and lys82 might constitute a bipartite localization signal (Dingwall and Laskey, Trends Biochem Sci.18:478–481, 1991). Mxi1 contains an acidic stretch at residues 135 to 180 (15 residues are glutamic or aspartic acid, predicted net charge of -14). The 340 noncoding region contained a stretch that contained substantial similarity to an expressed sequence tag found on a cDNA isolated from human brain (Adams et al., Nature 355:632–634, 1992) (FIG. 2); in particular, positions 1508–1958 contained a 443/450 nucleotide match (with one gap) with an expressed sequence tag (EST02043) from human brain (Adams et al., Nature 355:632–634, 1992).

The GenBank Accession Number for the Mxi1 sequence is L07648.

Association With Other Proteins

We tested whether Mxi1 interacted specifically with Max by repeating our initial interaction assays using a series of more closely related baits.

β-galactosidase levels were measured in cultures of yeast strain EGY48 that harbored pJK103, a medium-sensitive LexAop-lacZ reporter, into which plasmids that directed the synthesis of tagged Mxi1 and the listed baits were introduced. Measurements were performed in duplicate on three independent isolates, and the average value is shown in Table 1.

TABLE 1

| Bait Protein | Reporter Expression | | | |
|---|---|---|---|---|
| | Glucase | | Galactose | |
| | Leu | β-galactosidase | Leu | β-galactosidase |
| LexA-c-Myc-Cterm | − | <2 | + | 10 |
| LexA-Nax | − | <2 | +++ | 120 |
| LexA-Mxfl | + | 10 | + | 10 |
| LexA-Hairy | − | <2 | − | <2 |
| LexA-Id | − | <2 | − | <2 |
| LexA-n-MYC-bHLH-Zip | − | <2 | + | 8 |
| LexA-Da | − | <2 | − | <2 |

The results in Table 1 show that Mxi1 interacts strongly with Max, less strongly with the LexA-cMyc-Cterminus, and not at all with baits that contained other bHLH-Zip, bHLH, or b-Zip proteins, including LexA-Nmyc-Cterminus, LexA-Hairy, LexA-Id (HLH), and LexA-Da.

The specificity of the Mxi1/Myc interaction was confirmed by immunoprecipitation experiments with in vitro translated Mxi1 and potential interaction partners (described below). In vitro translated Mxi1 runs on an SDS gel with an apparent molecular weight of 32 kD, higher than the calculated molecular weight of 24.5 kD. Moreover, when Mxi1 is translated together with either form of the Max protein, $Max_{1-151}$ or $Max_{1-160}$, it can be precipitated by anti-Max antibodies, but when it is translated together with cMyc or nMyc, it cannot be precipitated with antisera directed against those proteins.

Site Recognition

Figure 4:
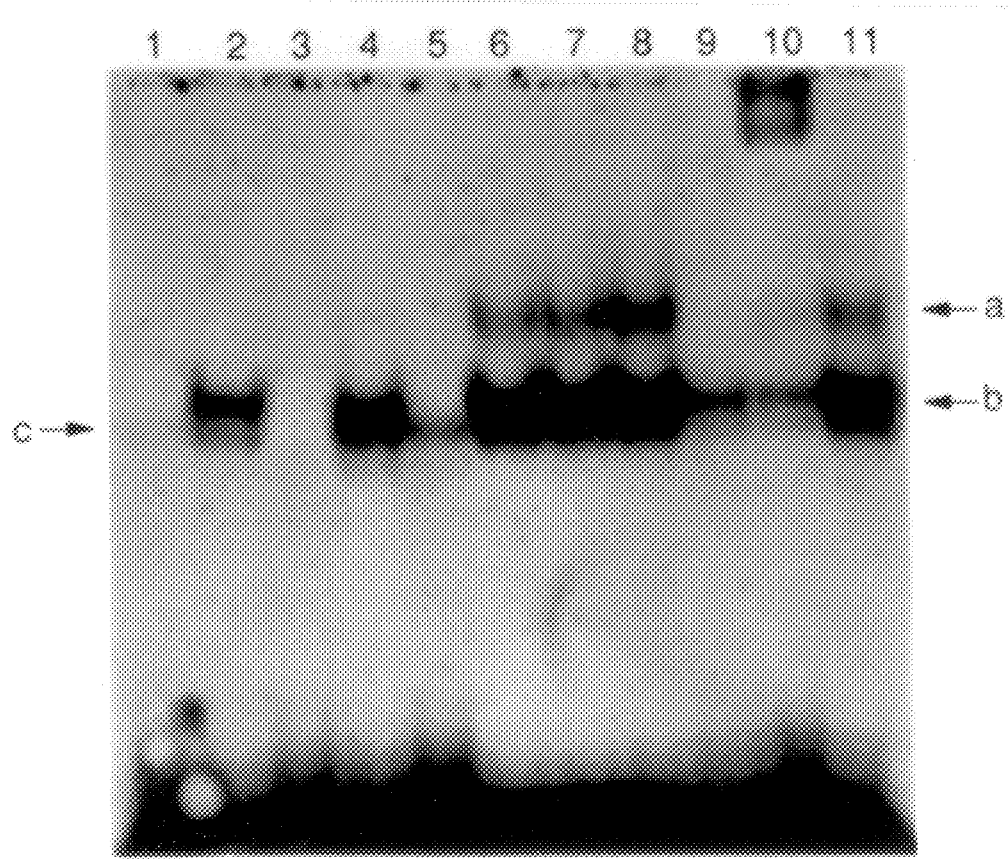
FIG. 4 demonstrates sequence specific binding by Mxi1 and Max. Binding assays used bacterially produced GST-Mxi1, full-length Max, and c-Myc bHLH-Zip (amino acids 342–439). The labeled oligonucleotide contained a consensus Myc-binding site. Binding reactions (20 μl) containing the indicated proteins and other reagents were performed, run on a 5% polyacrylamide gel, and subjected to autoradiography as described (see below), a, b, and c denote specific oligonucleotide-containing complexes. Lane 1, 300 ng of c-Myc bHLH-Zip; lane 2, 10 ng of Max; lane 3, 10 ng of GST-Mxi1; lane 4, 10 ng of Max, 300 ng of c-Myc bHLH-Zip; lane 5, 300 ng of Max, 300 ng of c-Myc bHLH-Zip; lane 6, 10 ng of Max, 10 ng of GST-Mxi1; lane 7, 10 ng of Max, 20 ng of GST-Mxi1: lane 8, 10 ng of Max, 50 ng of GST- Mxi1; lane 9, 10 ng of Max, 50 ng of GST-Mxi1, pretreated with 10 μl of 50% w/v glutathione-Sepharose beads, supernatant loaded on gel; lane 10, 10 ng of Max, 50 ng of GST-Mxi1, 1 μl of anti-Max antiserum; lane 11, 10 ng of Max, 50 ng of GST-Mxi1, 1 μl of control antiserum.

The above results suggest that Mxi1 interacts strongly and specifically with Max. The sequence of the Mxi1 bHLH-Zip region suggested that such Mxi1/Max heterodimers should bind the consensus Myc/Max recognition site. This was tested by assaying the ability of combinations of glutathione S-transferase (GST)-$Mxi1_{1-220}$, purified $Max_{1-151}$, and purified c-Myc bHLH-$Zip_{342-439}$ to retard the electrophoretic mobility of an oligonucleotide that contained the CACGTG Myc-Max consensus site (Halazonetis and Kandil, Science 255:464–466, 1991). These results are shown in FIG. 4. As expected, purified c-Myc bHLH-Zip caused the formation of a very small amount of retarded complex (FIG. 4, lane 1, complex c), purified Max caused the appearance of a larger amount of retarded complex of different mobility (lane 2, complex b), purified GST-Mxi1 did not give detectable amounts of retarded complex (lane 3), which we attribute to its inability to interact with itself (Table 1), and GST-Mxi1 and c-Myc bHLH-Zip did not form appreciable amounts of a new complex (lane 5). However, addition of GST-Mxi1 to Max resulted in the appearance of a complex of altered mobility (complex a, lane 5; the amount of this complex was increased with increasing amounts of GST-Mxi1 (lanes 7 and 8). This complex contained both Mxi1 and Max; treatment of the binding mixes with glutathione-Sepharose removed this complex quantitatively from the binding mix (lane 9), and treatment of the binding reactions with anti-Max antiserum resulted in the disappearance of most of the Mxi1-Max-DNA complex and its apparent supershift to a much less mobile DNA complex (lane 10). These results demonstrate that Mxi1 and Max complexes bind Myc-Max recognition sites.

Transcription Activation By Mxi1

The ability of Mxi1 to stimulate transcription was assayed. Plasmids directing the synthesis of LexA derivatives of Mxi1, Max, and cMyc were introduced into EGY40/ pJK103, and β-galactosidase assays were performed on cultures of independent transformants as described below. These results are shown in Table 2.

TABLE 2

| Potential Activator Protein | Reporter Expression (β-gal Units) |
|---|---|
| LexA-cMyc | 12 |
| LexA-Max | <2 |
| LexA-Mxil | <2 |

The results in Table 2 demonstrate that, unlike cMyc but like Max, Mxi1 is transcriptionally inert in this assay.

Mxi Expression

Figure 5:
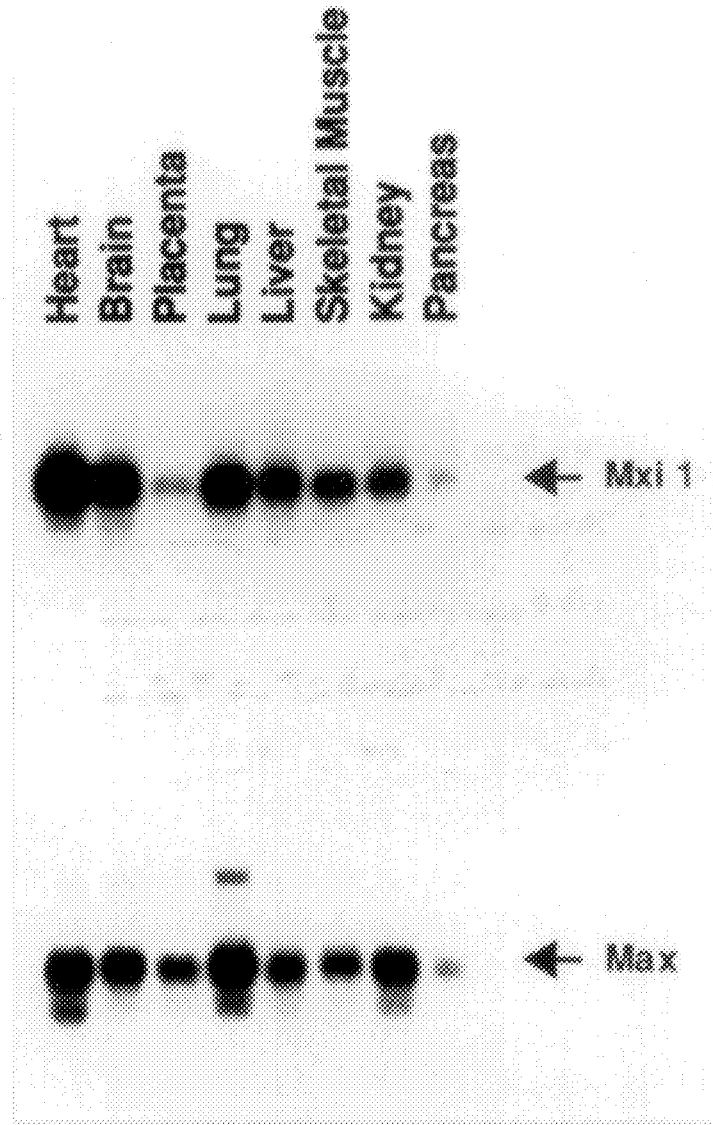
FIG. 5 shows the expression of Mxi1 and Max mRNA in different tissues. mRNA from different human tissues was probed with Mxi1, then stripped and reprobed with Max as described below (experimental procedures). Each lane contains 2 μg of polyA+ mRNA from (1) heart, (2) brain, (3) placenta, (4) lung, (5) liver, (6) skeletal muscle, (7) kidney, and (8) pancreas. Mxi1 mRNA runs with an apparent mobility of 3.2 kb, Max with an apparent mobility of 2 kb.

In order to determine in which tissues Mxi1 was expressed, a Northern blot containing 2 μg of polyA RNA from different human tissues (obtained from Clontech, Palo Alto, Calif.) was probed with Mxi1 and Max. This experiment revealed that Mxi1 mRNA was expressed in every tissue tested, with the highest levels in heart, brain, and lung (FIG. 5). The pattern of Max expression closely mirrors that of Mxi1 (FIG. 5). Northern analysis of Mxi1 MRNA expression in serum-starved and serum-stimulated WI38 human lung fibroblasts revealed that expression of the Mxi1 message was not induced by serum. Analysis of Mxi1 mRNA in synchronized populations of HeLa cells showed that its expression was also invariant through the cell cycle.

Mxi1 expression was next examined during differentiation of cells of the lymphoid lineage. We used such cells for three reasons: first, because down-regulation of Myc mRNA levels occurs upon differentiation; second, because constitutive expression of Myc can block their differentiation; and third, because we reasoned that changes in the differentiation state might affect the expression of other Myc-related messages.

In these experiments, RNA derived from two different premonocytic cell lines, U-937 and HL-60, was utilized. These lines are believed to correspond to different stages of monocytic development; U-937 is thought to be derived from a more determined cell type than HL-60. These lines can be induced to differentiate by a number of agents (reviewed in Harris and Ralph, J. Leukocyte Biol. 37:407–422, 1985); when so treated, U-937 differentiate along the monocytic pathway, while HL-60 differentiate into monocytes or granulocytes depending on the inducing agent. Expression of these messages was measured in myeloid cells for two reasons. First, because constitutive expression of c-Myc can block their differentiation (Freytag, Mol. Cell Biol. 8;1614–1624, 1988; Kume et al., J. Mol. Biol. 202:779–785, 1988); second, because down-regulation of c-Myc MRNA levels occurs during differentiation (Watanabe et al., Biochem. Biophys. Res. Comm. 126:999–1005, 1985; Gunji et al., J. Clin. Invest. 89:954–960, 1992), we thought that changes in the levels of myc-related messages might also occur during their differentiation.

Figure 6:
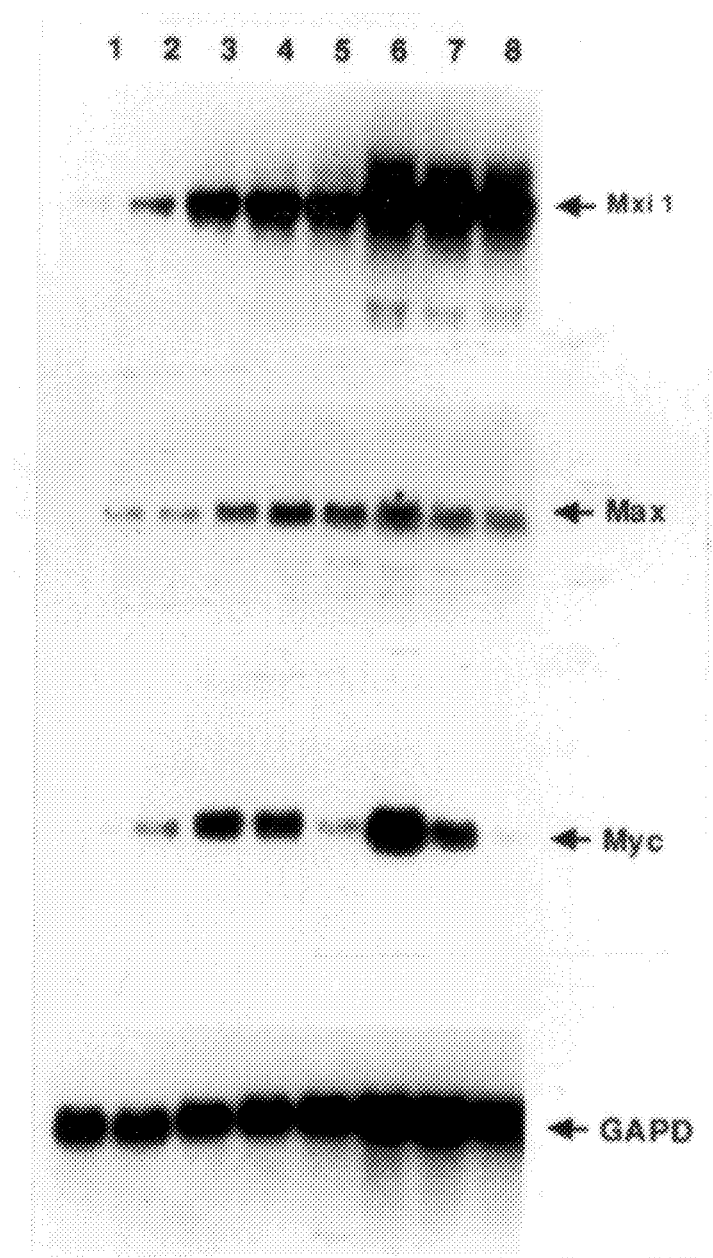
FIG. 6 shows the expression of Mxi1, Max, and Myc mRNA during differentiation. RNA was isolated from U937 and HL60 cells at different times after they were induced to differentiate with TPA (U-937) or retinoic acid (HL-60). 20 μg of RNA from cells from each time point was run on a gel and blotted onto a nylon membrane, which was probed successively with Mxi1, Max, cMyc, and human GAPD as described below (experimental procedures). Lane 1: U937, untreated; Lane 2: U937, 1 hour after TPA induction; Lane 3: U937, 3 hours after TPA induction; Lane 4: U937, 6 hours after TPA induction; Lane 5: U937, 12 hours after TPA induction; Lane 6: HL60, uninduced; Lane 7: HL60, 24 hours after retinoic acid induction; and Lane 8: HL60, 72 hours after retinoic acid induction.

As is shown in FIG. 6, treatment with TPA, the strongest inducer of U-937 differentiation, induces Mxi1 mRNA by a factor of about 20 (lanes 1–5). In order to verify that this induction was a consequence of differentiation, rather than a simple transcriptional response to TPA itself, Mxi1 message was examined in cells that were induced to differentiate with a number of other agents, including DMSO, retinoic acid, vitamin D3, tumor necrosis factor-α, and okadeic acid. Treatment with these agents also induced Mxi1 mRNA expression; the amount of Mxi1 induction by these agents paralleled their potency as inducers of differentiation (as determined by changes in morphology and induction of c-fms message).

In these cells, Max mRNA was low and its expression was not affected by treatment with TPA (FIG. 6). cMyc mRNA, as expected (Gunji et al., J. Clin. Invest. 89:954–960, 1992), was induced briefly, and then returned to a very low level (FIG. 6). By contrast, in HL60 cells, the basal level of Mxi1 and Max mRNA was much higher (lane 6). This level was not elevated in RNA from cells that were induced to differentiate with retinoic acid, although, as expected, the amount of c-myc mRNA was greatly reduced (lanes 7 and 8) (Watanabe et al., Biochem. Biophys. Res. Commun. 126:999–1005, 1985).

The Mxi1 Protein

We used the interaction trap to isolate Mxi1, a protein that interacts specifically with Max. The Mxi1 cDNA is 2400 nucleotides in length. Within it, there is an open reading frame that encodes a 220 amino acid protein, followed by a very large 340 untranslated region. The Mxi1 protein predicted from this open reading frame lacks a conspicuous nuclear localization signal, but contains a putative activation domain at its carboxy terminus and a bHLH-Zip motif at its amino terminus. The sequences of the Mxi1 bHLH-Zip is extremely similar to that of Myc family proteins; the basic region is identical in those residues thought to contact DNA. Helical wheel projections suggest that the Max/Mxi1 interaction may depend on a favorable ionic interaction between the leucine zippers of the two proteins.

We tested the function of Mxi1 in three ways. First, we used the interaction trap to further test the specificity of Mxi1's interaction with Max. We found that Mxi1 interacted very specifically with Max, and not with other related bHLH-Zip, bHLH, and bZIP proteins. We confirmed this result by immunoprecipitation experiments showing that in vitro translated Mxi1 interacted specifically with Max. Second, we performed gel retardation experiments that suggest Max/Mxi1 heterooligomers bind tightly to consensus Myc/Max binding sites. Third, we performed yeast transcription experiments. These experiments suggest that, like Max, Mxi1 is transcriptionally inert.

Finally, in an effort to understand Mxi1 function in vivo, we examined the expression of its mRNA. Mxi1 MRNA is expressed in all tissues, including ones, such as the brain, in which cMyc is not expressed. The cells in many of these tissues are terminally differentiated. To explore whether Mxi1 might be expressed in terminally differentiated cells, we monitored the expression of the mxi mRNA in myeloid cell lines whose c-myc mRNA levels were known to depend on their differentiation state. We found that, in U-937 cells that were provoked to undergo differentiation, the expression of mxi mRNA was strongly elevated at all times after induction, while expression of max and c-myc mRNA was elevated only slightly and at intermediate times. In HL-60 cells, which were derived from less determined cells, basal expression of Mxi1, Max and cMyc was high; when granulocyte differentiation was provoked by induction with retinoic acid, expression of Mxi and Max mRNA was not greatly altered, while, as expected, expression of c-myc mRNA was strongly reduced.

As assayed by interaction trap and gel retardation assays, Mxi1 interacts specifically with Max. The sequence of Mxi1 suggests one possible explanation for this specificity: a favorable ionic interaction between the Mxi1 and Max leucine zippers; ascribing an important function to this interaction seems reasonable given the contribution favorable leucine zipper interactions can make to dimerization of another bHLH-Zip protein, cMyc itself (Halazonetis and Kandil, Proc. Natl. Acad. Sci. USA 88:6162–6166, 1991). These experiments do not exclude the idea that Mxi1 might be able to form homodimers; if they did, they might be expected to associate with this same site.

We note that the interaction trap reveals a weak association between Mxi1 and Myc. We attribute our ability to detect this association to at least two causes: first, the relatively high intranuclear protein concentrations in this assay ($10^{-6}$M vs. $10^{-10}$M in typical immunoprecipitation experiments), and second, to our use of a sensitive LexAop-LEU2 reporter in the interaction trap system.

The experiments described herein identified four facts about Mxi1 that we believe are likely to be significant: its interaction with Max, its ability when complexed with Max to bind Myc/Max recognition sites, its lack of activation function, and its up-regulation, together with Max, in differentiating lymphoid cells.

These facts suggest that Mxi1 may affect Myc function negatively, in two ways, first by sequestering the Max that Myc needs to bind sites on DNA, and second, by forming inert complexes with Max that compete with transcriptionally active Myc/Max heterodimers for binding sites upstream of genes. According to this view, Mxi1 would normally inhibit Myc-dependent oncogenesis (i.e., act as an antioncoprotein), and, when its synthesis was induced during differentiation, would prevent Myc from activating transcription of its normal target genes. As such, the Mxi polypeptide is likely useful as an anti-cancer therapeutic (i.e., as a polypeptide which promotes differentiation). Its widespread expression in terminally differentiated cell lines (e.g., heart, brain, lung, liver, skeletal muscle, kidney, and pancreas) suggests that it may be useful for treating any number of different malignancies. Experiments described herein suggest its particular utility in treating hematopoietic malignancies, such as leukemias or lymphomas.

Moreover, because Mxi expression correlates with differentiation, at least in monocytic lineages, detection of a change in Mxi polypeptide cellular expression may be used as a diagnostic for detecting or monitoring malignant conditions or their treatment.

Mxi1 Fragments

Because Mxi1 likely exerts its effects by interacting with and sequestering cellular Max polypeptides, that portion of Mxi1 which binds Max may be useful in place of the full-length protein, for example, for therapeutic purposes. Such a Max-interacting fragment of Mxi1 preferably includes Mxi1's leucine zipper and may further include one or both of the surrounding helices. Referring to the sequence shown in FIG. 2 (SEQ ID NO: 1), Mxi1 fragments useful in the invention include (but are not limited to) amino acids 91–112 (comprising the Mxi1 leucine zipper) and amino acids 68–112 (comprising the Mxi1 leucine zipper and helix II).

The Mxi2 Protein

A second protein capable of interacting directly or indirectly with Max was isolated in the interaction trap screen described above. This protein was termed Mxi2, for Max Interactor 2. Mxi2 is a new protein kinase of the ERK type. Interaction trap experiments show that it also interacts, with equivalent affinity, with the cMyc oncoprotein itself.

Previous experiments have shown that ERK kinase acts at a site in Myc whose ability to be phosphorylated is necessary for Myc-mediated cell transformation; our experiments are thus consistent with the idea that Mxi2 is the ERK kinase whose action is necessary for Myc-dependent carcinogenesis (Alvarez et al., J. Biol. Chem. 266:15277–15285, 1991).

Characterization of Mxi2 (as described above) indicates that Mxi2 is a 297 residue protein whose sequence clearly identifies it as a member of the ERK protein kinase family (Crews et al., Cell Growth and Differentiation 3:135–142, 1992). The Mxi2 sequence is shown in FIG. 7 (SEQ ID NOS: 3 and 4) Its sequence is homologous to the other members of the ERK kinase family over the catalytic domain. Outside of that domain, Mxi2 exhibits no significant homology to known proteins. Mxi2's divergent regions may endow the protein with its specificity for Myc and Max. There is also some reason to believe that Mxi2 will be the ERK type kinase that kinases cJun (Alvarez et al., 1991, supra); if this is true, then Mxi2 may also may be necessary for Jun/Fos dependent cancers and signal transduction events.

Plasmids and Strains

Standard manipulations of E. coli, nucleic acids, and yeast were performed essentially as described in Ausubel et al., (Current Protocols in Molecular Biology, Greene Wiley-Interscience, New York 1989; Guthrie and Fink, Meth. Enzymol. 194:1–751, 1992). Bacterial strain KC8 (pyrF::Tn5, hsdR, leuB600, trpC9830, lacD74, strA, galK, hisB436) was used for the rescue of yeast plasmids as described (Hoffman and Winston, Gene 57:267–272, 1987). Transformants were collected on Trp-ampicillin plates.

Yeast strain EGY48 (MATa trp1 ura3 his3 LEU2::pLEU2-LexAop6) was constructed as follows. EGY12 (MATa trp1 ura2 LEU2::pLEU2-0 (ΔUASLEU2)) and EGY38 (as above but ::pLEU2-LexAop6) were first constructed using pLEU2-0 and pLEU2-LexAop6. These plasmids were linearized by digestion with ClaI within the LEU2 gene, and the DNA was introduced into U457 (MATa SUP53-a ade2-1 can1-100 ura3-52 trp1-1 [phi+]) by lithium acetate transformation (Ito et al., J. Bacter. 153:163–168, 1983); ura$^+$ colonies, which presumably contained the plasmid DNA integrated into LEU2, were selected. Several of these transformants were grown in YPD. Ura$^-$ cells were selected by plating these cultures on medium that contained 5-FOA (Ausubel et al., supra). Both plasmids carry a TY1 element. For each integration, some of the ura3$^-$ revertants were also trp1$^-$, suggesting that the URA3$^+$ marker was deleted in a homologous recombination event that involved the TY1 sequences on the LEU2 plasmids and the chromosomal TY1 element upstream of SUP53-a (Oliver et al., Nature 357:38–46, 1992). Trp$^-$ colonies from each integration, EGY12 (no LexA operators) and EGY38 (6 operators) were saved. These strains were then mated to GG100-14D (MATα his3 trp1 pho5). The resulting diploids were sporulated, and a number of random (MATα leu2$^-$ ura3$^-$ trp1$^-$ his3$^-$ GAL$^+$) spore products were recovered. EGY40 and EGY48 are products of this cross; EGY40 has no LexA operators, EGY48 has 6.

To make the baits strains, EGY48 was transformed with the reporter pJK103 (Kamens et al., Mol. Cell Biol. 10:2840–2847, 1990), which directs expression of a GAL1-LacZ gene from two high affinity ColE1 LexA operators (Ebina et al., J. Biol. Chem. 258:13258–13261, 1982). This reporter presumably binds 4 LexA dimers; it is about 5 times as sensitive to activation by LexA-containing proteins as is p1840 (Brent and Ptashne, Nature 312:612–615, 1984) although it is still not as responsive as the LexAop-LEU2 reporter in EGY48. Double tranformants were selected on Glucose Ura$^-$ His$^-$ plates.

All plasmids used to express the different baits, were based on pL202Pl (Ruden and Ptashne, Nature 350:250–252, 1991), which carries the HIS3$^+$ marker and a 2μ replicator. All baits contained, at their amino terminus, the LexA DNA binding domain and the C-terminal dimerization domain, which directs efficient operator occupancy by the bait (Golemis and Brent, Mol. Cell Biol. 12:3006–3014, 1992). LexA-Max contains the entire 151 residue form of the human Max protein (Blackwood and Eisenman, Science 251:1211–1217, 1991), LexA-cMyc-Cterm contains the 176 carboxy terminal amino acids of human c-Myc, but lacks the activation domains (Kato et al., Mol. Cell. Biol. 10:5914–5920, 1990. Both were cloned as EcoRI-BamHI fragments into pL202Pl after standard PCR amplification. (Vent Polymerase, New England Biolabs, Beverly, Mass.); in these constructions, no amino acids were introduced into the junction of these fusion proteins. LexA-Fus3 and LexA-Cln3, which contain the entire yeast FUS3 protein (Elion, Cell 60:649:664, 1990) and the entire CLN3 protein (Cross, Mol. Cell Biol. 8:4675–4684, 1988; Nase et al., EMBO J. 7:4335–4346, 1988) respectively, were constructed in the same manner, except that they were cloned as a BamHI fragment. These plasmids contained five amino acids (glu phe pro gly ile(SEQ ID. NO: 12)) inserted between lexA and the second amino acid of either Fus3 or Cln3. LexA-Bicoid contained residues 2–160 of the Drosophila bicoid gene product (Golemis and Brent, Mol. Cell Biol. 12:3006–3014, 1992), and LexA-nMyc contained the C-terminal 102 amino acids of the nmyc protein, including the bHLH-Zip. LexA-Id contained amino acids 64–133 of the human Id protein, LexA-Hairy contained the full length Drosophila hairy product, and LexA-Da contained residues 485–701 of the daughterless product.

Library-encoded proteins were expressed from pJG4-5, a member of a series of expression plasmids designed to be used in the interaction trap and to facilitate analysis of isolated proteins. These plasmids all carried the 2μ replicator to ensure high copy number in yeast, and the TRP1 marker. pJG4-5 was designed to possess the following features: a galactose-inducible promoter to allow conditional expression of the library proteins, an epitope tag to facilitate their detection, a nuclear localization signal to maximize their intranuclear concentration in order to increase the sensitivity of the selection, and a weak acid blob activation domain (Ma and Ptashne, Cell 51:113–119, 1987). This weak activation domain was chosen for two reasons: (i) because its activity is not subject to known regulation by yeast proteins as is the major GAL4 activation domain, and, more importantly, (ii) because it avoids the toxicity due to squelching or other mechanisms characteristic of strong activation domains (like GAL4) (Gill and Ptashne, Nature 334:721–724, 1988, Berger et al., Cell 70:251–265, 1992) which very likely restrict the number or type of interacting proteins recovered.

pJG4-5 was constructed as follows. An "expression cassette" containing the GAL1 promoter and the ADH1 terminator and a 345 nt insert that encoded a 107 amino acid moiety was inserted into pJG4-0, a plasmid that carries the TRP1 gene, the 2μ replicator, the pUC13 replication origin, and the ampicillin resistance gene. The pJG4-5 expression cassette directed the synthesis of fusion proteins, each of which carried at the amino terminus, amino to carboxy terminal, an ATG, an SV40 nuclear localization sequence (PPKKKRKVA) (SEQ ID NO: 5) (Kalderon et al., Cell 39:499–509, 1984), the B42 acid blob transcriptional activation domain (Ma and Ptashne, Cell 51:113–119, 1987) and the HA1 epitope tag (YPYDVPDYA) (SEQ ID NO: 6) (Green et al., Cell 28:477–487, 1980).

Library Construction

The activation-tagged yeast cDNA expression library was made from RNA isolated from serum grown, proliferating HeLa cells that were grown on plates to 70% confluence. Total RNA was extracted as described in Chomczynski and Sacchi (Anal. Biochem. 162:156–159, 1987), and polyA+ mRNA was purified on an oligodT-cellulose column. cDNA synthesis was performed according to Gubler and Hoffman (Gene 25:263–269, 1983) as modified by Huse and Hansen (Strategies 1:1–3, 1988) using a linker primer that contained, 540 to 3', an 18 nt polydT tract, an XhoI site, and a 25 nt long GA rich sequence to protect the XhoI site. To protect any internal XhoI sites, the first strand was synthesized in the presence of 5'-methyl-CTP (instead of CTP) with an RNAseH defective version of the Moloney virus reverse transcriptase (Superscript, BRL, Grand Island, N.Y.). For second strand synthesis, the mRNA/cDNA hybrid was treated with RNAseH and E. coli DNA polymerase I, and the resulting ends were made flush by sequential treatment with Klenow, Mung Bean exonuclease, and Klenow onto which EcoRI adaptors:

540 AATTCGGCACGAGGCG 340 (SEQ ID NO: 7)

340 GCCGTGCTCCGC 540 (SEQ ID NO: 8)

were ligated, and the cDNA was digested with XhoI. This DNA was further purified on a Sephacryl S-400 spin column in order to remove excess adaptor sequences, and fractionated on a 5–20% KoAc gradient. Fractions containing >700 bp cDNAs were collected, and approximately ⅓ of the cDNA was ligated into EcoRI- and XhoI-digested pJG4-5. This ligation mixture was introduced into E. coli SURE cells by electrophoration (Gene-Pulser, Bio-Rad, Hercules, Calif.) according to the manufacturer's instructions. $9.6 \times 10^6$ primary transformants were collected by scraping LB ampicillin plates. Colonies were pooled and grown in 6 liters of LB medium overnight (approximately three generations), and plasmid DNA was purified sequentially by standard techniques on two CsCl gradients. Digestion of transformants of individual library members with EcoR1 and XhoI revealed that >90% of the library members contained a cDNA insert whose typical size ranged between 1 kb–2 kb. Western blots of individual yeast transformants using the anti-hemagglutinin monoclonal antibody suggested that between ¼ and ⅓ of the members expressed fusion proteins.

Interaction Trap Screening

Yeast strain EGY48 was transformed with JK103 and a LexA-Max expression plasmid (termed PL-Max), and transformants were maintained under Ura and His selection. This strain was then transformed with the library according to the procedure described by Ito et al. (J. Bacter. 153:163–168, 1983), except that the cells were grown to a higher OD as described in Schiestl and Gietz (Curr. Genet 16:339–346, 1989) and single stranded carrier DNA was included in the transformation mix, also as described in Schiestl and Gietz (Curr. Genet 16:339–346, 1989). 750,000 primary yeast transformants were selected on Ura− His− Trp−/glucose plates, scraped, pooled and stored at −70°. Plating efficiency was determined on ura−his−trp−/Galactose plates, and five colony forming units/original transformant (i.e., approximately four million cells) were plated on Ura− His− Trp− Leu−/Galactose plates. Three days later, colonies appeared; these were restreaked and tested on Ura− His− Trp− Xgal/. Glucose and Ura− His− Trp− Xgal/Galactose plates. Plasmids from colonies that grew on leu− plates and turned blue on X-gal medium were isolated as described by Hoffman and Winston (1987; supra) and introduced into KC8 cells by electrophoration. Library plasmids was selected by growing the KC8 transformed cells on 1XA glucose Trp− Amp plates that contained uracil, histidine, leucine, and thiamine (Miller, Experiments in Molecular Genetics, Cold Spring Harbor Laboratory, New York, 1972).

cDNAs were first analyzed by restriction mapping using EcoRI, XhoI, and AluI enzymes and sorted into classes depending on their restriction map pattern. As least one representative cDNA from each class was partially sequenced by the dideoxy method using modified T7 DNA polymerase and a commercially available kit from US Biochemical, (Cleveland, Ohio). The full length cDNA clone for Mxi1 was isolated from a HeLa cDNA library in lambda ZapII (Stratagene, LaJolla, Calif.). One and a half million clones were screened using standard techniques (Ausubel et al., 1987; supra). Three positive clones were isolated, of which the longest contained a cDNA insert of 2.4 kb. Following phagemid rescue, the cDNA was completely sequenced by standard techniques using collapsed supercoiled DNA as template.

DNA-binding Assays

Gel retardation DNA binding assays were performed essentially as described in Papoulas et al., (J. Biol. Chem. 267:10470–10480, 1992). Purified Max and c-Myc bHLH-Zip (which contained residues 342–439 of human c-Myc) were made from recombinant E. coli by standard techniques. GST-Mxi1 was made as follows: a fragment that contained the entire coding sequence of Mxi1 was amplified using polymerase chain reaction, subcloned into pGEX-2T (Pharmacia), and transformed into DH5α cells. The fusion protein was induced and isolated as described (Smith and Corcoran, Current Protocols in Molecular Biology, Ausubel et al., eds., Greene Publishing and Wiley-Interscience, New York, 1989). A double-stranded oligonucleotide, 5'-GGAAGCAGACCACGTGGTCTGCTTCC-340 (SEQ ID NO: 9), that contained the CACGTG (SEQ ID NO: 10) consensus site was used. Approximately 0.5 μg of oligonucleotide was end labeled with [γ-$^{32}$P] ATP. Binding assays contained the indicated concentrations of purified Max, c-Myc bHLH-Zip, GST-Mxi1, and 0.5 ng of the labeled DNA probe. Assays were performed in a volume of 20 μl, so that the concentration of binding site was $2.5 \times 10^{-10}$M, the concentration of GST-Mxi1 ranged from $3 \times 10^{-9}$M (1 μl of Mxi1 in the binding reaction) to $1.5 \times 10-8$M (5 μl in the binding reaction), the concentration of Max was typically $5 \times 10^{-9}$, and the concentration of c-Myc bHLH-Zip, which had been purified after renaturation after guanidium treatment of an insoluble protein pellet, was $2.5 \times 10^{-7}$M. In these assays, the poly(dI-dC) often used as a nonspecific competitor was substituted with 200 ng (1200× molar excess over labeled oligonucleotide) of a nonspecific single-stranded oligonucleotide (5'-GTAATGCATCCAGTTC-3') (SEQ ID NO: 11) (as in Halazonetis and Kandil, Proc. Natl. Acad. Sci. USA 88:6162–6166, 1991). Binding was allowed to proceed for 20 min at room temperature in reaction buffer that contained 10 mM Tris (pH 7.4), 80 mM NaCl, 1 mM dithiothreitol, 5% glycerol. Where indicated, 1 μl of either control or anti-Max anterserum was added to the reactions. Binding mixtures were run on a 5% polyacrylamide gel (29:1, acrylamide: bisacrylamide) that contained 0.5× TBE buffer with 0.01% NP-40, with running buffer that contained 0.5× TBE and 0.05% NP-40, after which gels were dried and autoradiographed.

RNA Isolation and Northern Blot Analysis mRNA from differentiating U937 and HL60 cells was prepared by standard techniques. Cells were grown in RPMI 1640 containing 10% (for U937) or 15% (for HL60) heat inactivated fetal bovine serum, 100 units/ml penicillin, 100 μg/ml streptomycin, and 2 mM L-glutamine. U937 cells were treated with 32 nM TPA (Sigma, St. Louis, Mo.) for various times. Total RNA was isolated using the guanidine thiocyanate-cesium chloride method (Chirgwin et al., Biochemistry 18:5294–5304, 1979). 20 μg of RNA from each time point was analyzed by electrophoresis in 1% agarose-formaldehyde gels and transferred to nylon membranes (Zeta-Probe, Biorad, Hercules, Calif.), UV crosslinked, and hybridized as described (Ausubel et al., 1989; supra) to the following $^{32}$P-labeled DNA probes: (a) a 420 bp XhoI-XhoI fragment from pTZ8 corresponding to nucleotides 550 to 970 of Mxi1; (b) a 460 bp EcoR1-BamHI fragment from plasmid pSHmax carrying the full length coding sequence of Max; (c) a 1350 bp EcoR1-BamHI fragment from pSHmyc that contained the human cMyc coding sequence; and (d) a 1268 bp PstI-PstI fragment that carried the full length human glyceraldehyde-phosphate-dehydrogenase (GAPD) coding sequence (Tokunaga et al., Cancer Res. 47:5616–5618, 1987).

PolyPeptide Expression

In general, polypeptides according to the invention may be produced by transformation of a suitable host cell with all or part of an Mxi-encoding cDNA fragment (e.g., the cDNAs described above) in a suitable expression vehicle.

Those skilled in the field of molecular biology will understand that any of a wide variety of expression systems may be used to provide the recombinant protein. The precise host cell used is not critical to the invention. The Mxi polypeptide may be produced in a prokaryotic host (e.g., *E. coli*) or in a eukaryotic host (e.g., *Saccharomyces cerevisiae* or mammalian cells, e.g., COS 1, NIH 3T3, or HeLa cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors*: A Laboratory Manual (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding an Mxi polypeptide would be inserted into the pMAMneo vector in an orientation designed to allow expression. The recombinant Mxi protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, an Mxi polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the Mxi polypeptide is cloned into an expression vector which includes the dihydrofolate reductase (DHFR) gene. Integration of the plasmid and, therefore, the Mxi-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR$^-$ cells, ATCC Accession No. CRL 9096) are among the host cells preferred for DHFR selection of a stably-transfected cell line or DHFR-mediated gene amplification.

Once the recombinant Mxi protein is expressed, it is isolated, e.g., using affinity chromatography. In one example, an anti-Mxi antibody (e.g., produced as described herein) may be attached to a column and used to isolate the Mxi polypeptide. Lysis and fractionation of Mxi-harboring cells prior to affinity chromatography may be performed by standard methods (see, e.g., Ausubel et al., supra). Alternatively, an Mxi fusion protein, for example, an Mxi-maltose binding protein, an Mxi-β-galactosidase, or an Mxi-trpE fusion protein, may be constructed and used for isolation of Mxi protein (see, e.g., Ausubel et al., supra; New England Biolabs, Beverly, Mass.).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short Mxi fragments, can also be produced by chemical synthesis (e.g., by the methods described in Solid Phase Peptide Synthesis, 2nd ed., 1984 The Pierce Chemical Co., Rockford, Ill.).

These general techniques of polypeptide expression and purification can also be used to produce and isolate useful Mxi fragments or analogs (described below).

Anti-Mxi Antibodies

A human Mxi protein (or immunogenic fragments or analogues) may be used to raise antibodies useful in the invention; such polypeptides may be produced by recombinant or peptide synthetic techniques (see, e.g., Solid Phase Peptide Synthesis, suPra; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may be prepared using the Mxi polypeptides described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981; Ausubel et al., supra).

Once produced, polyclonal or monoclonal antibodies are tested for specific Mxi recognition by Western blot or immunoprecipitation analysis (by the methods described herein or in Ausubel et al., supra). Antibodies which specifically recognize a Mxi polypeptide are considered to be useful in the invention; such antibodies may be used, e.g., in an immunoassay to monitor the level of Mxi produced by a mammal.

Therapy

The Mxi1 polypeptide of the invention has been shown to interact with key regulators of human cell division, and its expression has been shown to correlate with cell differentiation. In addition, expression of Mxi1 in a wide variety of terminally differentiated tissues suggests a potentially general mechanism for its action. For these reasons, Mxi1 polypeptides present themselves as good candidates for anti-cancer therapeutics. Preferably, such a therapeutic is delivered as a sense or antisense RNA product, for example, by expression from a retroviral vector delivered, for example, to the bone marrow. General methods for introducing recombinant genes into, e.g., human cells for gene therapy are described in Miller (Human Gene Therapy 1:5–14, 1990); Friedman (Science 244:1275–1282, 1989); Eglitis and Anderson (BioTechniques 6:608–614, 1988); Tolstoshev and Anderson (Current Opinion in Biotechnology 1:55–61, 1990); Cornetta et al. (Nucleic Acid Research and Molecular Biology 36:311–322, 1987); Anderson (Science 226:401–409, 1984); Moen (Blood Cells 17:407–416, 1991); and Miller and Rosman (Biotechniques 7:980–990, 1989). Retroviral vectors are particularly well developed and have been used in a clinical setting (see, for example, Rosenberg et al., N. Engl. J. Med. 323:370, 1990). Alternatively, Mxi1 may be delivered locally, for example, directly to tumor cells, e.g., by retroviral transfer. As described above, for therapeutic purposes, full-length Mxi1 or, if desired, Max-interacting fragments of Mxi1 (e.g., fragments which include amino acids 91–112 or amino acids 68–112 of FIG. 2) may be utilized. Mxi1 gene therapy may also be combined with more traditional cancer therapies such as surgery, radiation, or chemotherapy.

Cancer Drug Screening

A cloned Mxi gene (e.g., Mxi1 or Mxi2) and, for example, the yeast interaction trap system described herein, may be used for the straightforward and inexpensive screening of a large number of drugs for those which alter the interaction between the Mxi protein and Max, and thus which are useful as cancer therapeutics. Drugs which increase Max:Mxi interaction would increase reporter gene expression in the interaction trap system, and conversely drugs which decrease Max:Mxi interaction would decrease reporter gene expression.

Alternatively, alterations in any Mxi phenotype may be assayed by any conventional assay which reflects an in vitro or in vivo Mxi activity. In one particular example, anti-cancer therapeutics may be identified using standard in vitro kinase assays and measuring biochemical changes in Mxi2's kinase activity.

Drugs identified by any of the above assays may be tested at a second level for efficacy in animal models, and drugs shown to be effective (for example, drugs which inhibit in vivo tumor formation or progression) may be used as anticancer therapeutics in humans according to their normal dosage and route of administration.

Detection of A Malignant Condition

Mxi polypeptides (e.g., Mxi1 or Mxi2) may also find diagnostic use in the detection or monitoring of cancerous conditions. For example, because Mxi1 expression is correlated with a differentiated cell state, a change in the level of Mxi production (e.g., a decrease in Mxi1 production) may indicate a malignant or pre-malignant condition. In general, levels of Mxi expression may be assayed by any standard technique. For example, Mxi expression may be monitored in a biological sample (e.g., a biopsy) by standard Northern blot analysis or may be aided by PCR (see, e.g., Ausubel et al., supra; PCR Technology: Principles and Applications for DNA Amplification, ed., H. A. Ehrlich, Stockton Press, NY). Diagnostic techniques are enabled by the provision of Mxi sequences (e.g., those in FIGS. 2 and 7; SEQ ID NOS: 1 and 3).

Alternatively, immunoassays may be used to detect Mxi protein in a biological sample. Mxi-specific polyclonal, or preferably monoclonal, antibodies (produced as described above) may be used in any standard immunoassay format (e.g., ELISA, Western blot, or RIA assay) to measure Mxi polypeptide levels; again comparison would be to wild type Mxi levels, and a change (e.g., a decrease) in Mxi production would be indicative of a malignant or pre-malignant condition. Examples of immunoassays are described, e.g., in Ausubel et al., supra. Immunohistochemical techniques may also be utilized for Mxi detection. For example, a tissue sample may be obtained from a patient, and a section stained for the presence of Mxi using an anti-Mxi antibody and any standard detection system (e.g., one which includes a secondary antibody conjugated to horseradish peroxidase). General guidance regarding such techniques can be found in, e.g., Bancroft and Stevens (Theory and Practice of Histological Techniques, Churchill Livingstone, 1982) and Ausubel et al. (supra).

The Mxi polypeptide is also useful for identifying that compartment of a mammalian cell where important cell division control functions occur. Antibodies specific for Mxi may be produced as described above. The normal subcellular location of the protein is then determined either in situ or using fractionated cells by any standard immunological or immunohistochemical procedure (see, e.g., Ausubel et al., supra; Bancroft and Stevens, Theory and Practice of Histological Technioues, Churchill Livingstone, 1982).

The methods of the instant invention may be used to reduce or diagnose the disorders described herein in any mammal, for example, humans, domestic pets, or livestock. Where a non-human mammal is treated, the Mxi polypeptide or the antibody employed is preferably specific for that species.

Other Embodiments

In other embodiments, the invention includes any protein which is substantially homologous to a human Mxi polypeptide (FIGS. 2 and 7, SEQ ID NOS: 1–4); such homologs include other substantially pure naturally occurring mammalian Mxi proteins as well as allelic variations; natural mutants; induced mutants; proteins encoded by DNA that hybridizes to the Mxi sequences of FIGS. 2 and 7 under high stringency conditions or low stringency conditions (e.g., washing at 2× SSC at 40° C. with a probe length of at least 40 nucleotides); and polypeptides or proteins specifically bound by antisera directed to a Mxi polypeptide, especially by antisera to the active site or to the Max binding domain of an Mxi protein. The term also includes chimeric polypeptides that include an Mxi fragment.

The invention further includes analogs of any naturally occurring Mxi polypeptide. Analogs can differ from the naturally occurring Mxi protein by amino acid sequence differences, by post-translational modifications, or by both. Analogs of the invention will generally exhibit at least 70%, more preferably 80%, even more preferably 90%, and most preferably 95% or even 99%, homology with all or part of a naturally occurring Mxi sequence. The length of comparison sequences will be at least 8 amino acid residues, preferably at least 24 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring Mxi polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, hereby incorporated by reference; or Ausubel et al., supra, hereby incorporated by reference). Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes Mxi polypeptide fragments. As used herein, the term "fragment" means at least 10 contiguous amino acids, preferably at least 30 contiguous amino acids, more preferably at least 50 contiguous amino acids, and most preferably at least 60 to 80 or more contiguous amino acids. Fragments of Mxi can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which exhibit biological activity (for example, the ability to interfere with mammalian cell division as assayed herein). Preferably, an Mxi polypeptide, fragment, or analog exhibits at least 10%, more preferably 30%, and most preferably, 70% or more of the biological activity of a full length naturally occurring Mxi polypeptide.

Other embodiments are within the following claims.

We claim:

1. A substantially pure polypeptide comprising the sequence of SEQ ID NO: 2.

2. An Mxi polypeptide produced by expression of a purified DNA comprising a sequence encoding the amino acid sequence of SEQ ID NO: 2.

3. A substantially pure polypeptide comprising amino acids 91–112 of the Mxi1 sequence of SEQ ID NO: 2.

4. A substantially pure polypeptide comprising amino acids 68–112 of the Mxi1 sequence of SEQ ID NO: 2.

5. A substantially pure polypeptide comprising the sequence of SEQ ID NO: 4.

6. An Mxi polypeptide produced by expression of a purified DNA comprising a sequence encoding the amino acid sequence of SEQ ID NO: 4.

* * * * *

UNITED STATES PATENT AND TRADEMARK OFFICE
CERTIFICATE OF CORRECTION

PATENT NO. 5,852,169
DATED December 22, 1998
INVENTORS Roger Brent and Antonis S. Zervos It is certified that error appears in the above-identified patent and that said Letters Patent is hereby corrected as shown below:

On the cover page, column 1, replace "Balckwood" with --Blackwood--.

On the cover page, column 2, replace "Prednergast" with --Prendergast--.

At col. 2, line 47, replace "1992" with --1992)--.

At col. 4, line 48, replace "3a" with --3A--.

At col. 4, line 64, replace "3b" with --3B--.

At col. 6, line 24, replace "540" with --5'--.

At col. 6, line 25, replace "340" with --3'--.

At col. 6, line 28, replace "3a" with --3A--.

At col. 6, line 50, replace "340" with --3'--.

At col. 12, line 30, replace "Cell 60:649:664" with --Cell 60:649-664--.

At col. 14, line 8, replace "Xgal/. Glucose" with --Xgal/Glucose--.

UNITED STATES PATENT AND TRADEMARK OFFICE
CERTIFICATE OF CORRECTION

PATENT NO. : 5,852,169
DATED : December 22, 1998
INVENTORS : Roger Brent and Antonis S. Zervos It is certified that error appears in the above-identified patent and that said Letters Patent is hereby corrected as shown below:

At col. 15, line 6, replace "0.5x" with --0.5X--.

At col. 15, line 8, replace "0.5x" with --0.5X--.

At col. 15, line 36, replace "PolyPeptide" with --Polypeptide--.

Signed and Sealed this

Eighth Day of February, 2000

Attest:

Attesting Officer

Q. TODD DICKINSON

Commissioner of Patents and Trademarks

SEQUENCE LISTING ( 1 ) GENERAL INFORMATION:

( i i i ) NUMBER OF SEQUENCES: 20

( 2 ) INFORMATION FOR SEQ ID NO: 1:

( i ) SEQUENCE CHARACTERISTICS:
        ( A ) LENGTH: 2417
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
AGATTATGAT    CGCCTGAGGC    CCCTCTCCTA    CCCAGATACC    GATGTTATAC    TGATGTGTTT         60

TTCCTTTTTT    TTTTTTTTTT    TTTAAGTAAT    TAAGGGTAGT    TAAATTATTT    AAAGTATACA        120

AAGTCCAAAC    AGCCAGGGGT    AAGGTCTCCA    AGAGGCCTTC    CCAGGGTAAG    GGAGTGCGGA        180

GAGGCCCCGG    TCGCCACCCG    CGGTGCCCAT    GGAGCGGGTG    AAGATGATCA    ACGTGCAGCG        240

TCTGCTGGAG    GCTGCCGAGT    TTTTGGAGCG    CCGGGAGCGA    GAGTGTGAAC    ATCGTACGCC        300

TCTTCATTCC    CGTCCATGCC    GAGCCCCCGA    CTGCAGCATT    CAAAGCCCCC    ACGGAGGTTG        360

AGCCGGGCAC    AGAAACACAG    CAGCGGGACG    AGCAACACCA    GCACTGCCAA    CAGATCTACA        420

CACAATGAGC    TGGAAAAGAA    TCGACGAGCT    CATCTGCGCC    TTTGTTTAGA    ACGCTTAAAA        480

GTTCTGATTC    CACTAGGACC    AGACTGCACC    CGGCACACAA    CACTTGGTTT    GCTCAACAAA        540

GCCAAAGCAC    ACATCAAGAA    ACTTGAAGAA    GCTGAAAGAA    AAAGCCAGCA    CCAGCTCGAG        600

AATTTGGAAC    GAGAACAGAG    ATTTTTAAAG    TGGCGACTGG    AACAGCTGCA    GGGTCCTCAG        660

GAGATGGAAC    GAATACGAAT    GGACAGCATT    GGATCAACTA    TTTCTTCAGA    TCGTTCTGAT        720

TCAGAGCGAG    AGGAGATTGA    AGTGGATGTT    GAAAGCACAG    AGTTCTCCCA    TGGAGAAGTG        780
```

-continued

| | | | | | | |
|---|---|---|---|---|---|---|
| GACAATATAA | GTACCACCAG | CATCAGTGAC | ATTGATGACC | ACAGCAGCCT | GCCGAGTATT | 840 |
| GGGAGTGACG | AGGGTTACTC | CAGTGCCAGT | GTCAAACTTT | CATTCACTTC | ATATAGAACC | 900 |
| CAGCATGACA | TAACAGTGCA | GGGCAAAATA | TTCACTGGGC | CAATTCAATA | CAAACAATCT | 960 |
| CTTAAATTGG | GTTCATGATG | CAGTCTCCTC | TTTAAAACAA | AACAAACAA | AACAAACTA | 1020 |
| TACTTGAACA | AAAGGGTCAG | AGGACCTGTA | TTTAAGCAAA | TACTTAGCAA | AAAGTGGGGC | 1080 |
| AGAGCTCCCA | AGGAGAACAA | ATATTCAGAA | TATTCATATT | GGAAAAATCA | CAATTTTTAA | 1140 |
| TGGCAGCAGA | AAACTTGTGT | GAAATTTTCT | TGATTTGAGT | TGATTGAGAA | GAGGACATTG | 1200 |
| GAGATGCCAT | CCTCTTTCTC | TTTTCTCGTT | TGCTCATACT | ACATTGAGTA | GACACATTTA | 1260 |
| AGGATGGGGT | TATGAACCCT | TCCTGAGCTT | TATGGTCCTA | AAAGCAAAAT | AAAAACTATT | 1320 |
| CGAATGAAAA | GACAAGAAAA | TCAGGTATTA | ATCTTGGATA | GCTAATAATG | AGCTATTAAA | 1380 |
| ACTCAGCCTG | GGACAGTTTA | TCATGAAGCC | TGTGGATGAT | CAATCCTTTA | TTATTATTTT | 1440 |
| TTTTTTTTGA | AAAAAGCTCA | TTTCATGCTC | TGCAAAAGGA | GAGACTCCCA | TGAAGCCTTT | 1500 |
| TGAAAGGGAT | CATCATGCAG | CTCAACTTTC | TGTTGGATTC | CATGCTAAGC | AAGCTAACCT | 1560 |
| TATCCTGCAT | TGTTAGCACT | AGGCACCCAG | CTGCCACCTC | TCCATCCTGC | TGCCCTTAGG | 1620 |
| CCACATGGGA | GCAGTCCATG | CATGACAGCC | TCTATCCTAC | AAGGCCTATG | AGTATGGATT | 1680 |
| GGGGGGGCCA | AAAGGAAAAA | GCTCCATGTG | CCTCTTTGTC | TGCGTGGGTC | AGAAGAGTTG | 1740 |
| TGCACGCAGA | TTAGCAGGCC | AAGGTCTGAG | CCACAGCAGC | ATTTTTATTT | CAGATTTTGA | 1800 |
| TAACTGTTTA | TATGTGTTGA | AAACCAAAAT | GACATCTTTT | TAAAGCTTAT | CCATAAAAAA | 1860 |
| AAATAGATGT | CTTTTATAGT | GGAAAAACAC | ATGGGGAAAA | AAATCATCTA | TTTTGATGCA | 1920 |
| GCATTTGATA | ATGATAAAAC | ACCTCACACC | TCACTCTTTA | TAGTGCACAA | AATGAATGAG | 1980 |
| GTCTGGGCTA | GGTAGAAAAA | GGGTCAATGC | TATTTTTGTT | TTTAGAATCA | TTACCTTTTA | 2040 |
| CCAGCTTTTA | ACCATCTGAT | ATCTATAGTA | GACACACTAT | CATAGTTAAC | ATAGTTAAGT | 2100 |
| TCAGCACTTG | TCTCATTTTA | ATGTAAAGAT | TTGCTTCCAT | TTTCCTACAG | GCAGTCTCTC | 2160 |
| TCTTCCTCAC | AGTCCCACTG | TGCAGGTGCT | ATTGTTACTC | TTACGAATAT | TTTCAGTAAT | 2220 |
| GTTATTTTCT | TCTAAGTGAA | ATTTCTAGCC | TGCACTTTGA | TGTCATGTGT | TCCCTTTGTC | 2280 |
| TTTCAAACTC | CAAGGTTCCC | CTGTGGCCCT | CTCCCTTACC | CTGGGAAGGC | CTCTTGGAGA | 2340 |
| CCTTACCCCT | GGCTGTTTGG | ACTTTGTATA | CTTTAAATAA | TTTAACTACC | CTTAATTACT | 2400 |
| TAAAAAAAAA | AAAAAA | | | | | 2417 |

(2) INFORMATION FOR SEQ ID NO: 2:

(i) SEQUENCE CHARACTERISTICS:
        (A) LENGTH: 220
        (B) TYPE: amino acid
        (C) STRANDEDNESS: Not Relevant
        (D) TOPOLOGY: linear (xi) SEQUENCE DESCRIPTION: SEQ ID NO: 2:

```
Met Pro Ser Pro Arg Leu Gln His Ser Lys Pro Pro Arg Arg Leu Ser
 1               5                  10                  15

Arg Ala Gln Lys His Ser Ser Gly Thr Ser Asn Thr Ser Thr Ala Asn
            20                  25                  30

Arg Ser Thr His Asn Glu Leu Glu Lys Asn Arg Arg Ala His Leu Arg
        35                  40                  45

Leu Cys Leu Glu Arg Leu Lys Val Leu Ile Pro Leu Gly Pro Asp Cys
    50                  55                  60
```

| Thr | Arg | His | Thr | Thr | Leu | Gly | Leu | Leu | Asn | Lys | Ala | Lys | Ala | His | Ile |
| 65  |     |     |     | 70  |     |     |     |     | 75  |     |     |     |     |     | 80  |

| Lys | Lys | Leu | Glu | Glu | Ala | Glu | Arg | Lys | Ser | Gln | His | Gln | Leu | Glu | Asn |
|     |     |     |     | 85  |     |     |     |     | 90  |     |     |     |     | 95  |     |

| Leu | Glu | Arg | Glu | Gln | Arg | Phe | Leu | Lys | Trp | Arg | Leu | Glu | Gln | Leu | Gln |
|     |     |     | 100 |     |     |     |     | 105 |     |     |     |     | 110 |     |     |

| Gly | Pro | Gln | Glu | Met | Glu | Arg | Ile | Arg | Met | Asp | Ser | Ile | Gly | Ser | Thr |
|     |     | 115 |     |     |     |     | 120 |     |     |     |     | 125 |     |     |     |

| Ile | Ser | Ser | Asp | Arg | Ser | Asp | Ser | Glu | Arg | Glu | Glu | Ile | Glu | Val | Asp |
|     |     | 130 |     |     |     |     | 135 |     |     |     |     | 140 |     |     |     |

| Val | Glu | Ser | Thr | Glu | Phe | Ser | His | Gly | Glu | Val | Asp | Asn | Ile | Ser | Thr |
| 145 |     |     |     |     | 150 |     |     |     |     | 155 |     |     |     |     | 160 |

| Thr | Ser | Ile | Ser | Asp | Ile | Asp | Asp | His | Ser | Ser | Leu | Pro | Ser | Ile | Gly |
|     |     |     |     | 165 |     |     |     |     | 170 |     |     |     |     | 175 |     |

| Ser | Asp | Glu | Gly | Tyr | Ser | Ser | Ala | Ser | Val | Lys | Leu | Ser | Phe | Thr | Ser |
|     |     |     | 180 |     |     |     |     | 185 |     |     |     |     | 190 |     |     |

| Tyr | Arg | Thr | Gln | His | Asp | Ile | Thr | Val | Gln | Gly | Lys | Ile | Phe | Thr | Gly |
|     |     | 195 |     |     |     |     | 200 |     |     |     |     | 205 |     |     |     |

| Pro | Ile | Gln | Tyr | Lys | Gln | Ser | Leu | Lys | Leu | Gly | Ser |
|     | 210 |     |     |     |     | 215 |     |     |     |     | 220 |

( 2 ) INFORMATION FOR SEQ ID NO: 3:

( i ) SEQUENCE CHARACTERISTICS:
        ( A ) LENGTH: 1200
        ( B ) TYPE: nucleic acid
        ( C ) STRANDEDNESS: single
        ( D ) TOPOLOGY: linear ( x i ) SEQUENCE DESCRIPTION: SEQ ID NO: 3:

```
AGTGAATTGT AATACGACTC ACTATAGGGC GAATTGGGTA CCGGGCCCCC CCTCGAGGTC     60
GACGGTATCG ATAAGCTTGA TATCGAATTC CCGCGCGCGC GGAGTCTGCG GGGTCGCGGC    120
AGCCGCACCT GCGCGGGCGA CCAGCGCAAG GTCCCCGCCC GGCTGGGCGG GCAGCAAGGG    180
CCGGGGAGAG GGTGCGGGTG CAGGCGGGGG CCCCACAGGG CCACCTTCTT GCCCGGCGCG    240
TGCCGCTGGA AAATGTCTCA GGAGAGGCCC ACGTTCTACC GGCAGGAGCT GAACAAGACA    300
ATCTGGAGG TGCCCGAGCG TTACCAGAAC CTGTCTCCAG TGGGCTCTGG CGCCTATGGC    360
TCTGTGTGTG CTGCTTTTGA CACAAAAACG GGGTTACGTG TGGCAGTGAA GAAGCTCTCC    420
AGACCATTTC AGTCCATCAT TCATGCGAAA AGAACCTACA GAGAACTGCG GTTACTTAAA    480
CATATGAAAC ATGAAAATGT GATTGGTCTG TTGGACGTTT TTACACCTGC AAGGTCTCTG    540
GAGGAATTCA ATGATGTGTA TCTGGTGACC CATCTCATGG GGCAGATCT GAACAACATT    600
GTGAAATGTC AGAAGCTTAC AGATGACCAT GTTCAGTTCC TTATCTACCA AATTCTCCGA    660
GGTCTAAAGT ATATACATTC AGCTGACATA ATTCACAGGG ACCTAAAACC TAGTAATCTA    720
GCTGTGAATG AAGACTGTGA GCTCAAGATT CTGGATTTTG GACTGGCTCG GCACACAGAT    780
GATGAAATGA CAGGCTACGT GGCCACTAGG TGGTACAGGG CTCCTGAGAT CATGCTGAAC    840
TGGATGCATT ACAACCAGAC AGTTGATATT TGGTCAGTGG GATGCATAAT GGCCGAGCTG    900
TTGACTGGAA GAACATTGTT TCCTGGTACA GACCATATTG ATCAGTTGAA GCTCATTTTA    960
AGACTCGTTG GAACCCCAGG GGCTGAGCTT TTGAAGAAAA TCTCCTCAGA GTCTGCAAGT   1020
TTCTATATTC AGTCTTTGAC TCAGATGCCG AAGATGAACT TTGCGAATGT ATTTATTGGT   1080
GCCAATCCCC TGGGTAAGTT GACCATATAT CCTCACCTCA TGGATATTGA ATTGGTTATG   1140
ATATAAATTG GGGATTTGAA GAAGAGTTTC TCCTTTTGAC CAAATAAAGT ACCATTATGA   1200
```

( 2 ) INFORMATION FOR SEQ ID NO: 4:

( i ) SEQUENCE CHARACTERISTICS:
        ( A ) LENGTH: 297
        ( B ) TYPE: amino acid
        ( C ) STRANDEDNESS: Not Relevant
        ( D ) TOPOLOGY: linear ( x i ) SEQUENCE DESCRIPTION: SEQ ID NO: 4:

```
Met  Ser  Gln  Glu  Arg  Pro  Thr  Phe  Tyr  Arg  Gln  Glu  Leu  Asn  Lys  Thr
 1              5                        10                       15
Ile  Trp  Glu  Val  Pro  Glu  Arg  Tyr  Gln  Asn  Leu  Ser  Pro  Val  Gly  Ser
               20                  25                       30
Gly  Ala  Tyr  Gly  Ser  Val  Cys  Ala  Ala  Phe  Asp  Thr  Lys  Thr  Gly  Leu
          35                       40                       45
Arg  Val  Ala  Val  Lys  Lys  Leu  Ser  Arg  Pro  Phe  Gln  Ser  Ile  Ile  His
     50                       55                  60
Ala  Lys  Arg  Thr  Tyr  Arg  Glu  Leu  Arg  Leu  Leu  Lys  His  Met  Lys  His
 65                 70                       75                            80
Glu  Asn  Val  Ile  Gly  Leu  Leu  Asp  Val  Phe  Thr  Pro  Ala  Arg  Ser  Leu
                    85                       90                       95
Glu  Glu  Phe  Asn  Asp  Val  Tyr  Leu  Val  Thr  His  Leu  Met  Gly  Ala  Asp
               100                      105                      110
Leu  Asn  Asn  Ile  Val  Lys  Cys  Gln  Lys  Leu  Thr  Asp  Asp  His  Val  Gln
          115                      120                      125
Phe  Leu  Ile  Tyr  Gln  Ile  Leu  Arg  Gly  Leu  Lys  Tyr  Ile  His  Ser  Ala
     130                      135                      140
Asp  Ile  Ile  His  Arg  Asp  Leu  Lys  Pro  Ser  Asn  Leu  Ala  Val  Asn  Glu
145                      150                      155                           160
Asp  Cys  Glu  Leu  Lys  Ile  Leu  Asp  Phe  Gly  Leu  Ala  Arg  His  Thr  Asp
               165                      170                      175
Asp  Glu  Met  Thr  Gly  Tyr  Val  Ala  Thr  Arg  Trp  Tyr  Arg  Ala  Pro  Glu
               180                      185                      190
Ile  Met  Leu  Asn  Trp  Met  His  Tyr  Asn  Gln  Thr  Val  Asp  Ile  Trp  Ser
          195                      200                      205
Val  Gly  Cys  Ile  Met  Ala  Glu  Leu  Leu  Thr  Gly  Arg  Thr  Leu  Phe  Pro
     210                      215                      220
Gly  Thr  Asp  His  Ile  Asp  Gln  Leu  Lys  Leu  Ile  Leu  Arg  Leu  Val  Gly
225                      230                      235                           240
Thr  Pro  Gly  Ala  Glu  Leu  Leu  Lys  Lys  Ile  Ser  Ser  Glu  Ser  Ala  Ser
               245                      250                      255
Phe  Tyr  Ile  Gln  Ser  Leu  Thr  Gln  Met  Pro  Lys  Met  Asn  Phe  Ala  Asn
          260                      265                      270
Val  Phe  Ile  Gly  Ala  Asn  Pro  Leu  Gly  Lys  Leu  Thr  Ile  Tyr  Pro  His
          275                      280                      285
Leu  Met  Asp  Ile  Glu  Leu  Val  Met  Ile
290                      295
```

( 2 ) INFORMATION FOR SEQ ID NO: 5:

( i ) SEQUENCE CHARACTERISTICS:
        ( A ) LENGTH: 9
        ( B ) TYPE: amino acid
        ( C ) STRANDEDNESS: Not Relevant
        ( D ) TOPOLOGY: linear ( x i ) SEQUENCE DESCRIPTION: SEQ ID NO: 5:

Pro Pro Lys Lys Lys Arg Lys Val Ala
1               5

(2) INFORMATION FOR SEQ ID NO: 6:

(i) SEQUENCE CHARACTERISTICS:
        (A) LENGTH: 9
        (B) TYPE: amino acid
        (C) STRANDEDNESS: Not Relevant
        (D) TOPOLOGY: linear (xi) SEQUENCE DESCRIPTION: SEQ ID NO: 6:

Tyr Pro Tyr Asp Val Pro Asp Tyr Ala
1               5

(2) INFORMATION FOR SEQ ID NO: 7:

(i) SEQUENCE CHARACTERISTICS:
        (A) LENGTH: 16
        (B) TYPE: nucleic acid
        (C) STRANDEDNESS: single
        (D) TOPOLOGY: linear (xi) SEQUENCE DESCRIPTION: SEQ ID NO: 7:

AATTCGGCAC GAGGCG                                                  16

(2) INFORMATION FOR SEQ ID NO: 8:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 8:

GCCGTGCTCC GC                                                      12

(2) INFORMATION FOR SEQ ID NO: 9:

(i) SEQUENCE CHARACTERISTICS:
        (A) LENGTH: 26
        (B) TYPE: nucleic acid
        (C) STRANDEDNESS: single
        (D) TOPOLOGY: linear (xi) SEQUENCE DESCRIPTION: SEQ ID NO: 9:

GGAAGCAGAC CACGTGGTCT GCTTCC                                  26

(2) INFORMATION FOR SEQ ID NO: 10:

(i) SEQUENCE CHARACTERISTICS:
        (A) LENGTH: 6
        (B) TYPE: nucleic acid
        (C) STRANDEDNESS: single
        (D) TOPOLOGY: linear (xi) SEQUENCE DESCRIPTION: SEQ ID NO: 10:

CACGTG                                                                  6

(2) INFORMATION FOR SEQ ID NO: 11:

(i) SEQUENCE CHARACTERISTICS:
        (A) LENGTH: 16
        (B) TYPE: nucleic acid
        (C) STRANDEDNESS: single
        (D) TOPOLOGY: linear (xi) SEQUENCE DESCRIPTION: SEQ ID NO: 11:

GTAATGCATC CAGTTC 16

(2) INFORMATION FOR SEQ ID NO: 12:

(i) SEQUENCE CHARACTERISTICS:
        (A) LENGTH: 5
        (B) TYPE: amino acid
        (C) STRANDEDNESS: Not Relevant
        (D) TOPOLOGY: linear (xi) SEQUENCE DESCRIPTION: SEQ ID NO: 12:

```
Glu  Phe  Pro  Gly  Ile
 1                    5
```

(2) INFORMATION FOR SEQ ID NO: 13:

(i) SEQUENCE CHARACTERISTICS:
        (A) LENGTH: 80
        (B) TYPE: amino acid
        (C) STRANDEDNESS: Not Relevant
        (D) TOPOLOGY: linear (xi) SEQUENCE DESCRIPTION: SEQ ID NO: 13:

```
Asn  Arg  Ser  Thr  His  Asn  Glu  Leu  Glu  Lys  Asn  Arg  Arg  Ala  His  Leu
 1                    5                   10                        15
Arg  Leu  Cys  Leu  Glu  Arg  Leu  Lys  Val  Leu  Ile  Pro  Leu  Gly  Pro  Asp
              20                       25                        30
Cys  Thr  Arg  His  Thr  Thr  Leu  Gly  Leu  Leu  Asn  Lys  Ala  Lys  Ala  His
              35                       40                        45
Ile  Lys  Lys  Leu  Glu  Glu  Ala  Glu  Arg  Lys  Ser  Gln  His  Gln  Leu  Glu
         50                       55                   60
Asn  Leu  Glu  Arg  Glu  Gln  Arg  Phe  Leu  Lys  Trp  Arg  Leu  Glu  Gln  Leu
 65                       70                       75                        80
```

(2) INFORMATION FOR SEQ ID NO: 14:

(i) SEQUENCE CHARACTERISTICS:
        (A) LENGTH: 80
        (B) TYPE: amino acid
        (C) STRANDEDNESS: Not Relevant
        (D) TOPOLOGY: linear (xi) SEQUENCE DESCRIPTION: SEQ ID NO: 14:

```
Lys  Arg  Arg  Thr  His  Asn  Val  Leu  Glu  Arg  Gln  Arg  Arg  Asn  Glu  Leu
 1                    5                   10                        15
Lys  Leu  Ser  Phe  Phe  Ala  Leu  Arg  Asp  Gln  Ile  Pro  Glu  Val  Ala  Asn
              20                       25                        30
Asn  Glu  Lys  Ala  Pro  Lys  Val  Val  Ile  Leu  Lys  Lys  Ala  Thr  Glu  Tyr
              35                       40                        45
Val  Leu  Ser  Ile  Gln  Ser  Asp  Glu  His  Arg  Leu  Ile  Ala  Glu  Lys  Glu
         50                       55                   60
Gln  Leu  Arg  Arg  Arg  Arg  Glu  Gln  Leu  Lys  His  Lys  Leu  Glu  Gln  Leu
 65                       70                       75                        80
```

(2) INFORMATION FOR SEQ ID NO: 15:

(i) SEQUENCE CHARACTERISTICS:
        (A) LENGTH: 80
        (B) TYPE: amino acid
        (C) STRANDEDNESS: Not Relevant
        (D) TOPOLOGY: linear (xi) SEQUENCE DESCRIPTION: SEQ ID NO: 15:

```
Lys  Arg  Arg  Thr  His  Asn  Val  Leu  Glu  Arg  Gln  Arg  Arg  Asn  Glu  Leu
 1                  5                        10                       15

Lys  Arg  Ser  Phe  Phe  Ala  Leu  Arg  Asp  Gln  Ile  Pro  Glu  Leu  Glu  Asn
               20                       25                  30

Asn  Glu  Lys  Ala  Pro  Lys  Val  Val  Ile  Leu  Lys  Lys  Ala  Thr  Ala  Tyr
          35                       40                       45

Tyr  Leu  Ser  Val  Gln  Ala  Glu  Glu  Gln  Lys  Leu  Ile  Ser  Glu  Glu  Asp
     50                       55                       60

Leu  Leu  Arg  Lys  Arg  Glu  Gln  Leu  Lys  His  Lys  Leu  Glu  Gln  Leu
 65                 70                       75                       80
```

(2) INFORMATION FOR SEQ ID NO: 16:

(i) SEQUENCE CHARACTERISTICS:
        (A) LENGTH: 80
        (B) TYPE: amino acid
        (C) STRANDEDNESS: Not Relevant
        (D) TOPOLOGY: linear (xi) SEQUENCE DESCRIPTION: SEQ ID NO: 16:

```
Arg  Arg  Arg  Asn  His  Asn  Ile  Leu  Glu  Arg  Gln  Arg  Arg  Asn  Asp  Leu
 1                  5                        10                       15

Arg  Ser  Ser  Phe  Leu  Thr  Leu  Arg  Asp  His  Val  Pro  Glu  Leu  Val  Lys
               20                       25                  30

Asn  Glu  Lys  Ala  Ala  Lys  Val  Val  Ile  Leu  Lys  Lys  Ala  Thr  Glu  Tyr
          35                       40                       45

Val  His  Ser  Leu  Gln  Ala  Glu  Glu  His  Gln  Leu  Leu  Leu  Glu  Lys  Glu
     50                       55                       60

Lys  Leu  Gln  Ala  Arg  Gln  Gln  Leu  Leu  Lys  Lys  Ile  Glu  His  Ala
 65                 70                       75                       80
```

(2) INFORMATION FOR SEQ ID NO: 17:

(i) SEQUENCE CHARACTERISTICS:
        (A) LENGTH: 80
        (B) TYPE: amino acid
        (C) STRANDEDNESS: Not Relevant
        (D) TOPOLOGY: linear (xi) SEQUENCE DESCRIPTION: SEQ ID NO: 17:

```
Lys  Arg  Lys  Asn  His  Asn  Phe  Leu  Glu  Arg  Lys  Arg  Arg  Asn  Asp  Leu
 1                  5                        10                       15

Arg  Ser  Arg  Phe  Leu  Ala  Leu  Arg  Asp  Gln  Val  Pro  Thr  Leu  Ala  Ser
               20                       25                  30

Cys  Ser  Lys  Ala  Pro  Lys  Val  Val  Ile  Leu  Ser  Lys  Ala  Leu  Glu  Tyr
          35                       40                       45

Leu  Gln  Ala  Leu  Val  Gly  Ala  Glu  Lys  Arg  Met  Ala  Thr  Glu  Lys  Arg
     50                       55                       60

Gln  Leu  Arg  Cys  Arg  Gln  Gln  Leu  Gln  Lys  Arg  Ile  Ala  Tyr  Leu
 65                 70                       75                       80
```

(2) INFORMATION FOR SEQ ID NO: 18:

(i) SEQUENCE CHARACTERISTICS:
        (A) LENGTH: 79
        (B) TYPE: amino acid
        (C) STRANDEDNESS: Not Relevant
        (D) TOPOLOGY: linear (xi) SEQUENCE DESCRIPTION: SEQ ID NO: 18:

```
Lys  Arg  Ala  His  His  Asn  Ala  Leu  Glu  Arg  Lys  Arg  Arg  Asp  His  Ile
 1                  5                        10                       15
```

Lys Asp Ser Phe His Ser Leu Arg Asp Ser Val Pro Ser Leu Gln Gly
            20                  25                  30

Gln Lys Ala Ser Lys Ala Gln Ile Leu Asp Lys Ala Thr Glu Tyr Ile
        35              40                  45

Gln Tyr Met Arg Arg Lys Asn His Thr His Gln Gln Asp Ile Asp Asp
    50              55                  60

Leu Lys Arg Gln Asn Ala Leu Leu Glu Gln Gln Val Arg Ala Leu
65              70                  75

( 2 ) INFORMATION FOR SEQ ID NO: 19:

( i ) SEQUENCE CHARACTERISTICS:
      ( A ) LENGTH: 79
      ( B ) TYPE: amino acid
      ( C ) STRANDEDNESS: Not Relevant
      ( D ) TOPOLOGY: linear ( x i ) SEQUENCE DESCRIPTION: SEQ ID NO: 19:

Arg Arg Glu Ile Ala Asn Ser Asn Glu Arg Arg Arg Met Gln Ser Ile
1               5                   10                  15

Asn Ala Gly Phe Gln Ser Leu Lys Thr Leu Lys Pro His Thr Asp Gly
            20                  25                  30

Glu Lys Leu Ser Lys Ala Ala Ile Leu Gln Gln Thr Ala Glu Tyr Ile
        35              40                  45

Phe Ser Leu Glu Gln Glu Lys Thr Arg Leu Leu Gln Gln Asn Thr Gln
    50              55                  60

Leu Lys Arg Phe Ile Gln Glu Leu Ser Gly Ser Ser Pro Lys Arg
65              70                  75

( 2 ) INFORMATION FOR SEQ ID NO: 20:

( i ) SEQUENCE CHARACTERISTICS:
      ( A ) LENGTH: 84
      ( B ) TYPE: amino acid
      ( C ) STRANDEDNESS: Not Relevant
      ( D ) TOPOLOGY: linear ( x i ) SEQUENCE DESCRIPTION: SEQ ID NO: 20:

Lys Lys Asp Asn His Asn Leu Ile Glu Arg Arg Arg Arg Phe Asn Ile
1               5                   10                  15

Asn Asp Arg Ile Lys Glu Leu Gly Thr Leu Ile Pro Lys Ser Ser Asp
            20                  25                  30

Pro Gln Met Arg Trp Asn Lys Gly Thr Ile Leu Lys Ala Ser Val Asp
        35              40                  45

Tyr Ile Arg Lys Leu Gln Lys Glu Gln Gln Ser Lys Asp Arg Leu Glu
    50              55                  60

Ser Arg Gln Arg Ser Leu Glu Gln Ala Asn Arg Ser Leu Gln Leu Arg
65              70                  75              80

Ile Gln Glu Leu